US010849614B2

(12) United States Patent
Arnold et al.

(10) Patent No.: US 10,849,614 B2
(45) Date of Patent: Dec. 1, 2020

(54) ARTICULATION CONTROL FEATURES FOR SUTURING INSTRUMENT

(71) Applicant: Ethicon LLC, Guaynabo, PR (US)

(72) Inventors: Bradley A. Arnold, Mason, OH (US); David T. Martin, Milford, OH (US); Kevin M. Montgomery, Morrow, OH (US)

(73) Assignee: Ethicon LLC, Guaynabo, PR (US)

( * ) Notice: Subject to any disclaimer, the term of this patent is extended or adjusted under 35 U.S.C. 154(b) by 196 days.

(21) Appl. No.: 15/983,407

(22) Filed: May 18, 2018

(65) Prior Publication Data

US 2019/0350579 A1 Nov. 21, 2019

(51) Int. Cl.
*A61B 17/04* (2006.01)
*A61B 17/29* (2006.01)
*A61B 17/00* (2006.01)

(52) U.S. Cl.
CPC .... *A61B 17/0469* (2013.01); *A61B 17/00234* (2013.01); *A61B 17/0483* (2013.01); *A61B 17/2909* (2013.01); *A61B 2017/00398* (2013.01); *A61B 2017/2932* (2013.01)

(58) Field of Classification Search
CPC .......... A61B 17/0469; A61B 17/06133; A61B 2017/00367; A61B 2017/00407; A61B 2017/00473; A61B 2017/0608; A61B 2017/2927; A61B 2017/2946; A61B 2090/0811; A61B 17/2909; A61M 25/0136; A61M 25/0105
See application file for complete search history.

(56) References Cited

U.S. PATENT DOCUMENTS

| | | | |
|---|---|---|---|
| 8,702,732 B2 | 4/2014 | Woodard, Jr. et al. | |
| 9,168,037 B2 | 10/2015 | Woodard, Jr. et al. | |
| 9,186,142 B2 | 11/2015 | Fanelli et al. | |
| 9,357,998 B2 | 6/2016 | Martin et al. | |
| 9,375,212 B2 | 6/2016 | Martin et al. | |
| 9,474,522 B2 | 10/2016 | Deck et al. | |
| 9,888,914 B2 | 2/2018 | Martin et al. | |
| 2015/0351747 A1* | 12/2015 | Martin .............. | A61B 17/0469 606/145 |
| 2016/0367238 A1* | 12/2016 | Deck ................. | A61B 17/0469 |
| 2017/0112488 A1* | 4/2017 | Baxter, III ......... | A61B 17/0469 |

* cited by examiner

*Primary Examiner* — George J Ulsh
(74) *Attorney, Agent, or Firm* — Frost Brown Todd LLC

(57) ABSTRACT

A surgical instrument for treating a patient includes a shaft assembly and a body assembly. The shaft assembly includes a proximal end portion, a distal end portion, and an articulation joint operable to selectively articulate the distal end portion relative to the proximal end portion. The body assembly includes a joint drive assembly, an actuator, and a joint stabilizer. The joint drive assembly is operatively connected to the articulation joint and configured to actuate the articulation to thereby articulate the distal end portion relative to the proximal end portion. The actuator is configured to actuate the joint drive assembly for articulating the articulation joint. The joint stabilizer includes a detent abutment and a detent notch configured to releasably capture the joint drive assembly and thereby inhibit articulation of the distal end portion of the shaft assembly relative to the proximal end portion of the shaft assembly.

20 Claims, 30 Drawing Sheets

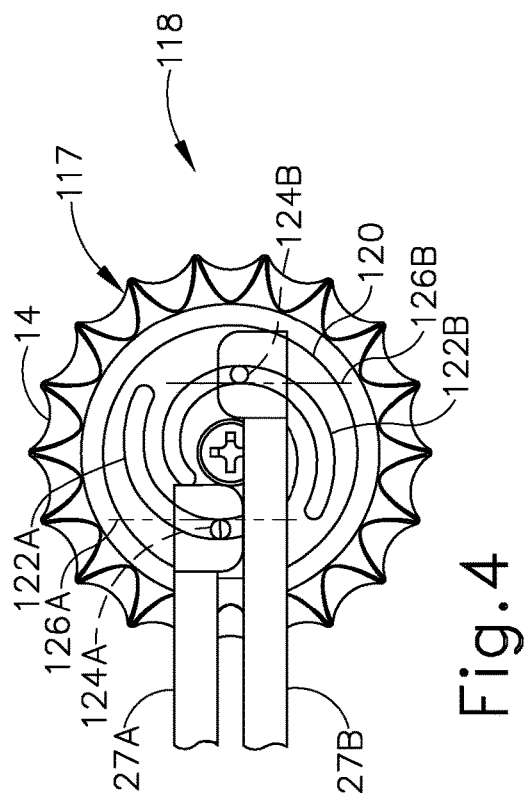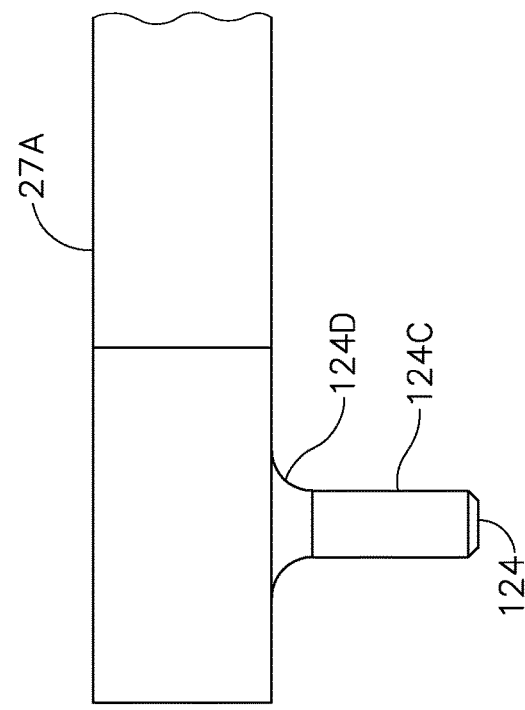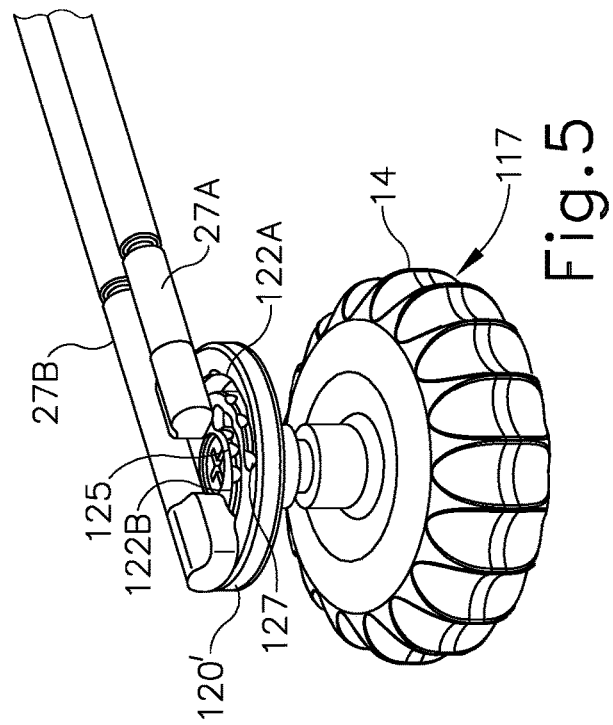

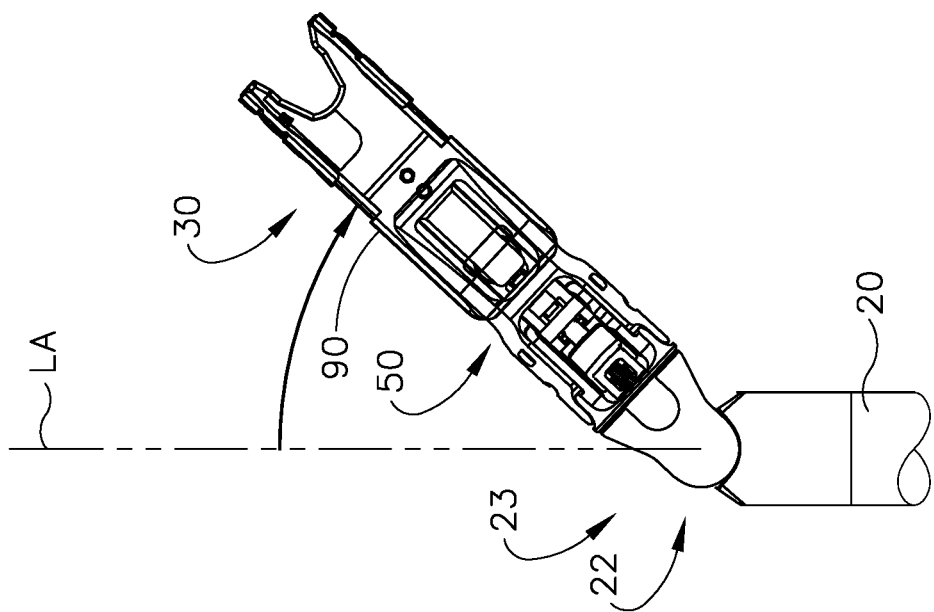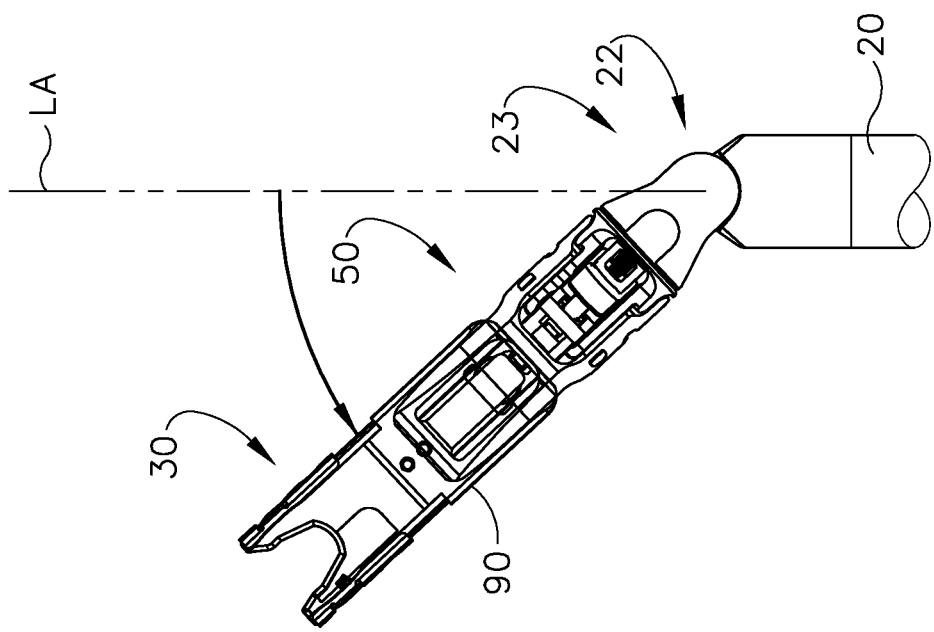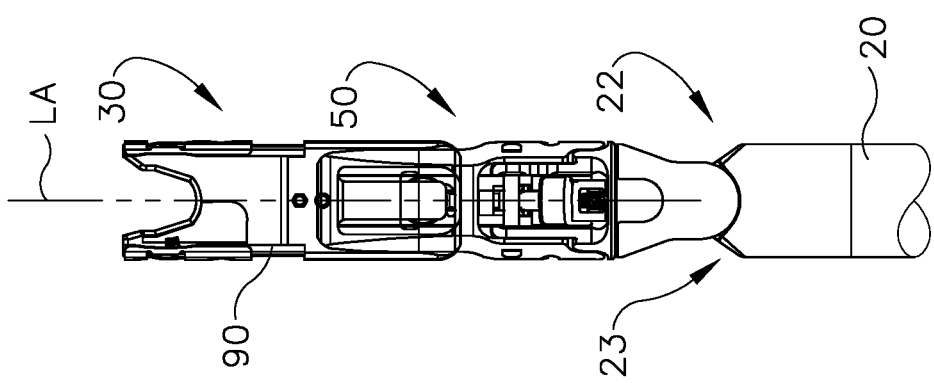

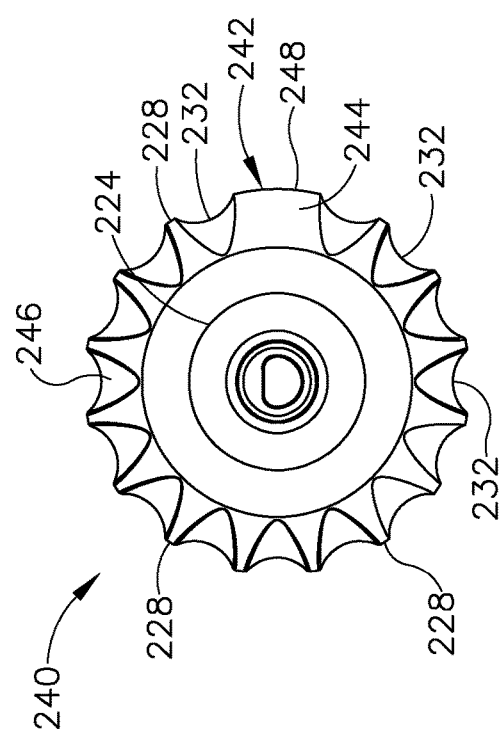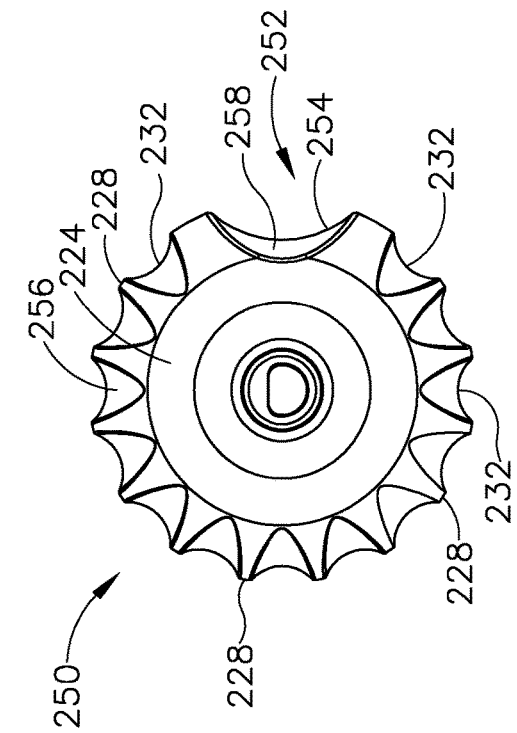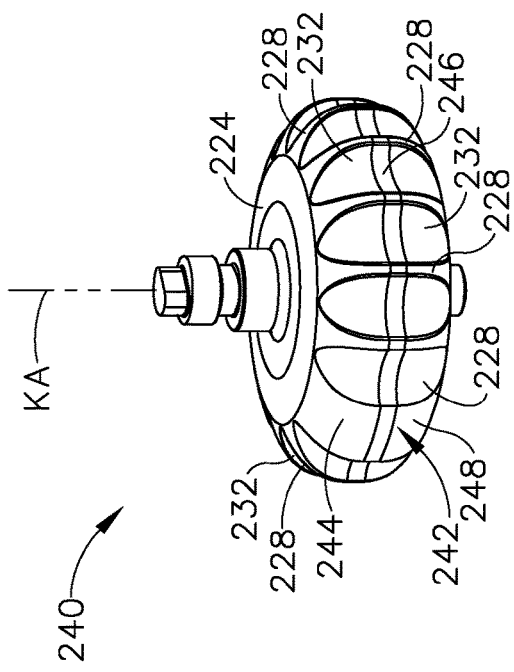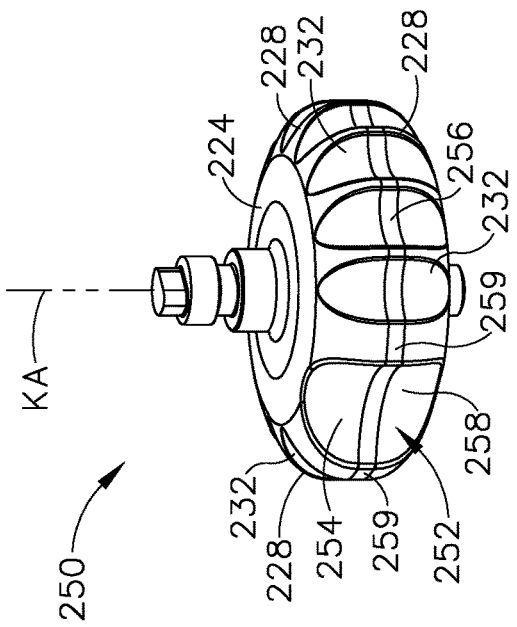

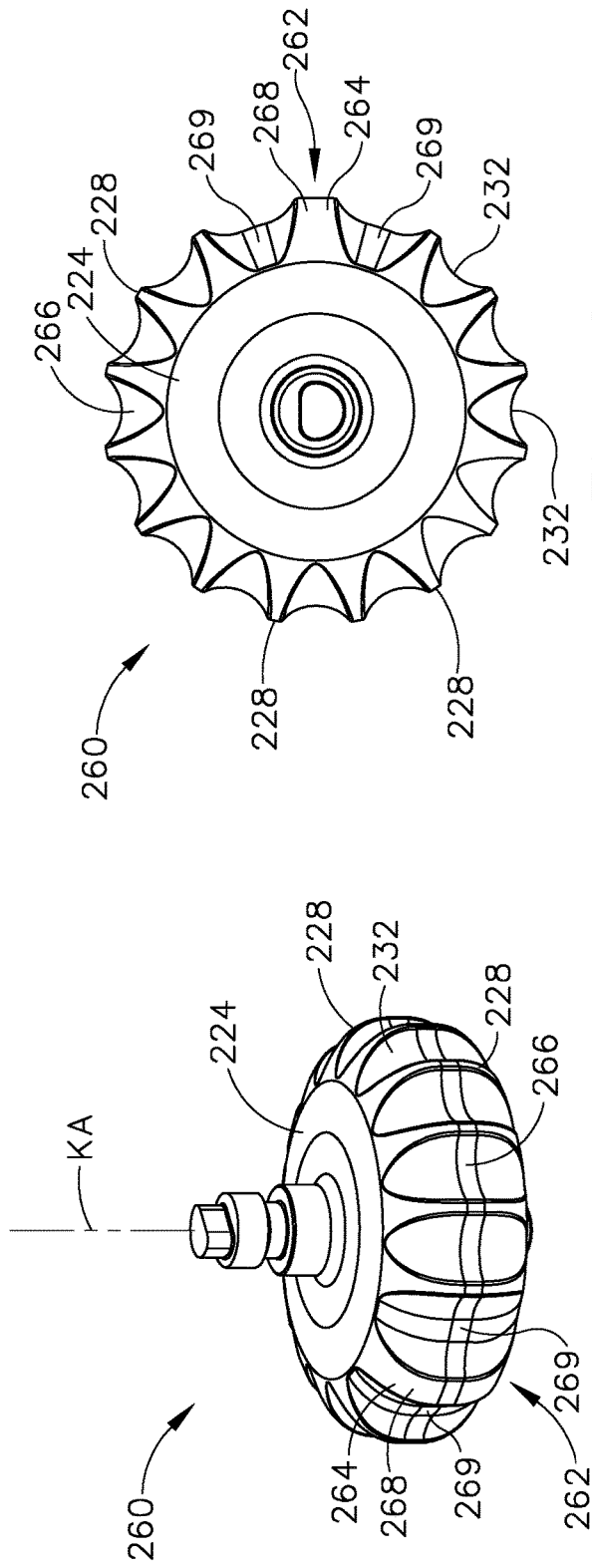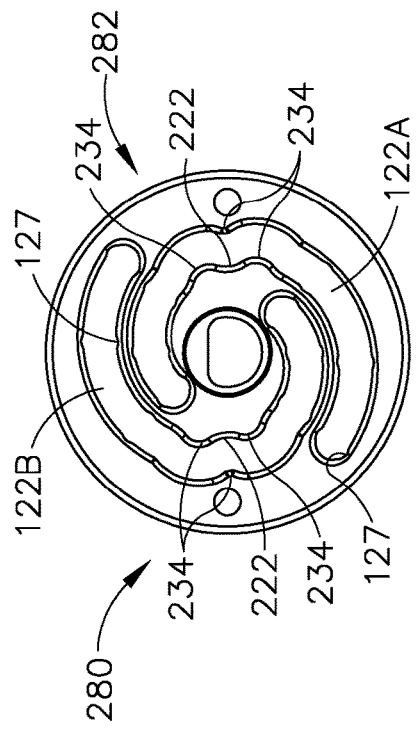

ARTICULATION CONTROL FEATURES FOR SUTURING INSTRUMENT

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pat. No. 9,168,037, entitled "Laparoscopic Suture Device with Asynchronous In-Line Needle Movement," issued Oct. 27, 2015, the disclosure of which is incorporated by reference herein; U.S. Pat. No. 9,357,998, entitled "Circular Needle Applier with Articulating and Rotating Shaft," issued Jun. 7, 2016, the disclosure of which is incorporated by reference herein; and U.S. Pat. No. 9,474,522, entitled "Jawed Receiver for Needle Cartridge," issued Oct. 25, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4 depicts a top plan view of a first example of an articulation control assembly of the handle assembly of FIG. 3 with a first exemplary rotary knob and a first exemplary disk;

FIG. 5 depicts a perspective view of the articulation control assembly of FIG. 4 with a second exemplary disk;

FIG. 6 depicts a side elevational view of an articulation rod and follower of the articulation control assembly of FIG. 4;

FIG. 7A depicts a top plan view of the cartridge receiving assembly of FIG. 2, the cartridge of FIG. 1, and the shaft assembly of the instrument of FIG. 1, with the cartridge receiving assembly aligned with the longitudinal axis of the shaft assembly;

FIG. 7B depicts a top plan view of the cartridge receiving assembly of FIG. 2, the cartridge of FIG. 1, and the shaft assembly of the instrument of FIG. 1, with the cartridge receiving assembly deflected in a first direction away from the longitudinal axis of the shaft assembly by the articulation control assembly of FIG. 4; and FIG. 7C depicts a top plan view of the cartridge receiving assembly of FIG. 2, the cartridge of FIG. 1, and the shaft assembly of the instrument of FIG. 1, with the cartridge receiving assembly deflected in a second direction away from the longitudinal axis of the shaft assembly by the articulation control assembly of FIG. 4;

FIG. 13 depicts a perspective view of a third exemplary rotary knob having a second example of a knob position indicator for use with the articulation control assembly of FIG. 4;

FIG. 14 depicts a top plan view of the rotary knob with the knob position indicator of FIG. 13;

FIG. 15 depicts a perspective view of a fourth exemplary rotary knob having a third example of a knob position indicator for use with the articulation control assembly of FIG. 4;

FIG. 16 depicts a top plan view of the rotary knob with the knob position indicator of FIG. 15;

FIG. 17 depicts a perspective view of a fifth exemplary rotary knob having a fourth example of a knob position indicator for use with the articulation control assembly of FIG. 4;

FIG. 18 depicts a top plan view of the rotary knob with the knob position indicator of FIG. 17;

FIG. 19 a perspective view of a fourth exemplary disk having a second example of a detent position indicator for use with the articulation control assembly of FIG. 4;

Figure 1:
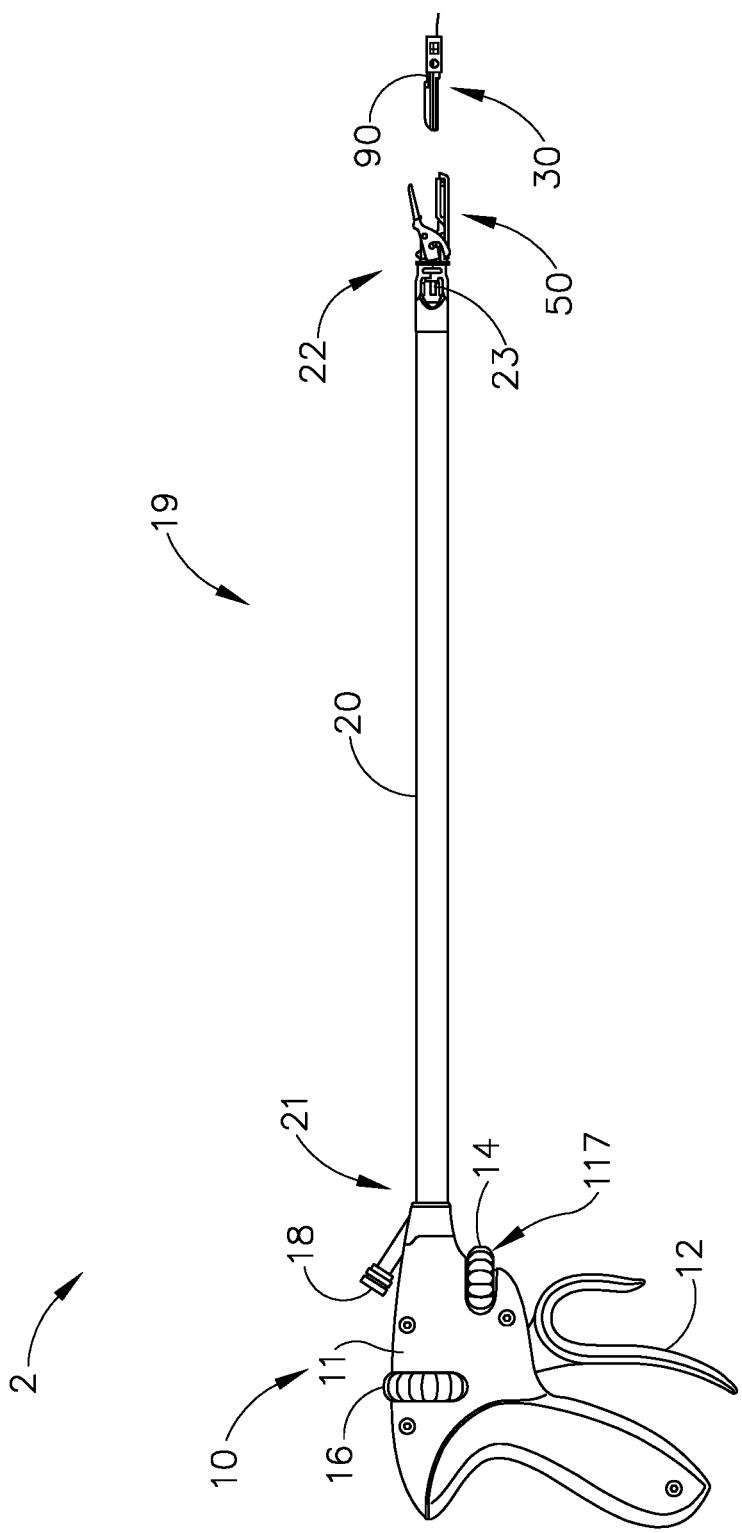
FIG. 1 depicts a side view of an exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal", "distal", "upper", "lower", "top", and "bottom" are defined herein relative to an operator or other operator grasping a surgical instrument having a distal surgical end effector. The term "proximal" refers the position of an element closer to the operator or other operator, and the term "distal" refers to the position of an element closer to the surgical end effector of the surgical instrument and further away from the operator or other operator. The terms "top" and "upper" refer to the position of the element closer to a top of the surgical instrument when viewed by the user from above, and the terms "bottom" and "lower" refer to the position of the element closer to a bottom of the surgical instrument when viewed by the user from below. As such, proximal and distal portions are generally in longitudinal opposition as described herein, whereas upper and lower portions are generally in transverse opposition as described herein.

I. Overview of Exemplary Surgical Suturing Instrument

FIG. 1 illustrates an example of a surgical suturing instrument (2). Instrument (2) comprises a handle assembly (10) and a shaft assembly (19) having an elongate shaft (20) extending from a distal end portion (22) to a proximal end portion (21) thereof. Distal end portion (22) includes a cartridge receiving assembly (50), which is operable to receive a needle applier cartridge (30). Shaft (20) defines a longitudinal axis extending from proximal end portion (21) to distal end portion (22). Handle assembly (10) is connected to proximal end portion (21) of shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to distal end portion (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first user input member (12), shown here as a trigger that pivots between opened and closed positions, may be used to selectively actuate needle applier cartridge (30). The trigger may be spring biased to return the trigger to its open position. A first example of an articulation control assembly (117) includes a second user input member (14), shown here as a first exemplary rotary knob, may be used to selectively articulate shaft (20). A third user input member (16), shown here as a rotary knob, may be used to selectively rotate needle applier cartridge (30) about shaft (20). Of course, the number, type, configuration, and operation of input members (12, 14, 16) may vary.

Figure 2:
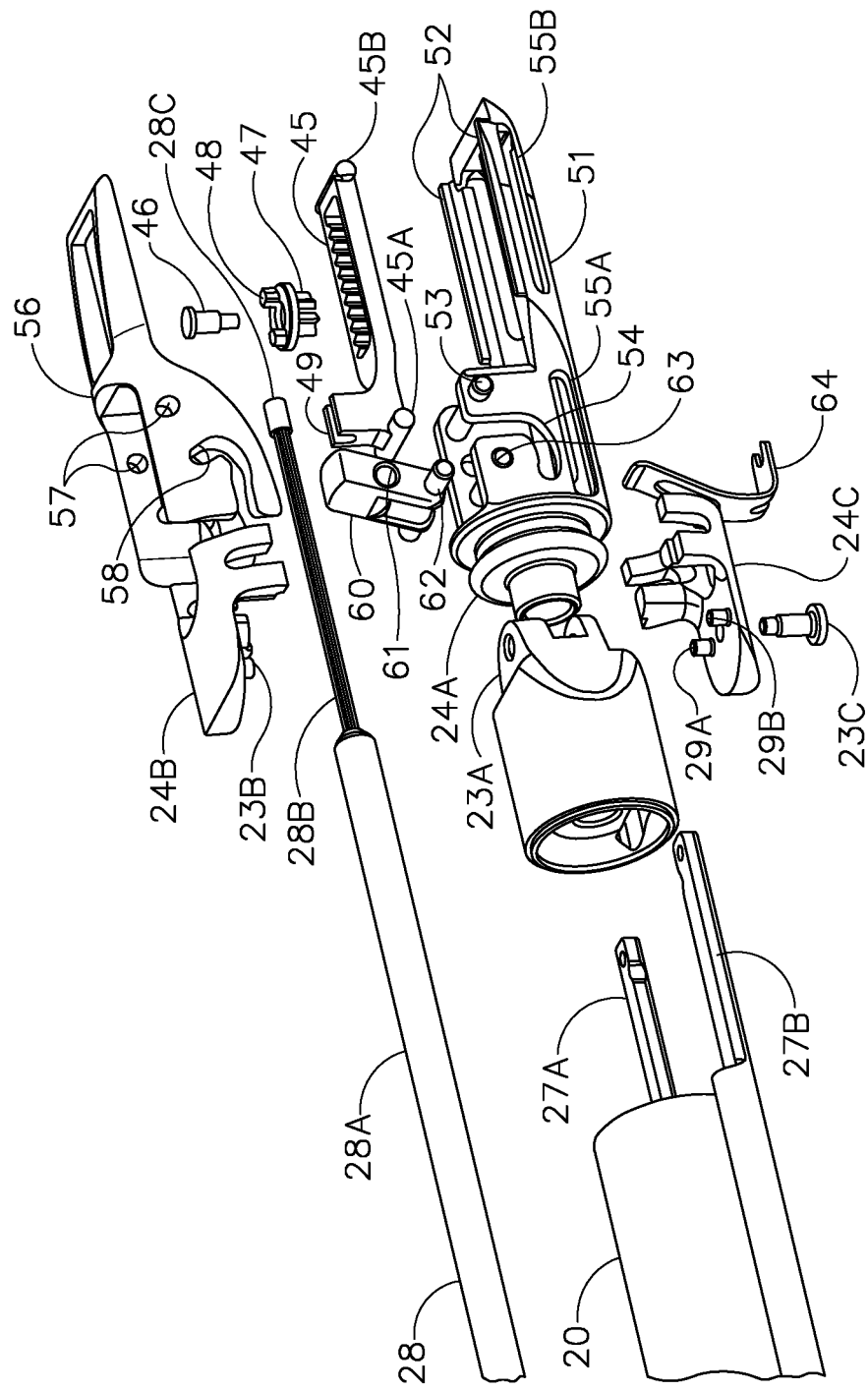
FIG. 2 depicts top perspective exploded view of a cartridge receiving assembly of the instrument of FIG. 1.

FIG. 2 illustrates an exploded view of cartridge receiving assembly (50) (see FIG. 1) of the present example. Distal end portion (22) (see FIG. 1) of shaft (20) comprises an articulation joint (23) and a rotational bearing (24). Articulation joint (23) (see FIG. 1) includes a knuckle (23A) that receives pins (23B, 23C), which are connected to bearing supports (24B, 23C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to rotary knob (14) to opposingly push and pull rods (27A, 27B). In other words, rotary knob (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, 29B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by a pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first user input member (12) and to third user input member (16). Actuation of first user input member (12) will impart axial push and pull loads on drive rod (28) to longitudinally reciprocate rack (45) and thereby actuate needle applier cartridge (30). Actuation of third user input member (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIG. 2, cartridge receiving assembly (50) of this example has upper and lower jaws (56, 51) that are operable to transition between an open configuration and a closed configuration. In the closed configuration, jaws (56, 51) are operable to receive and retain cartridge body (90). In the closed configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received in hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3:
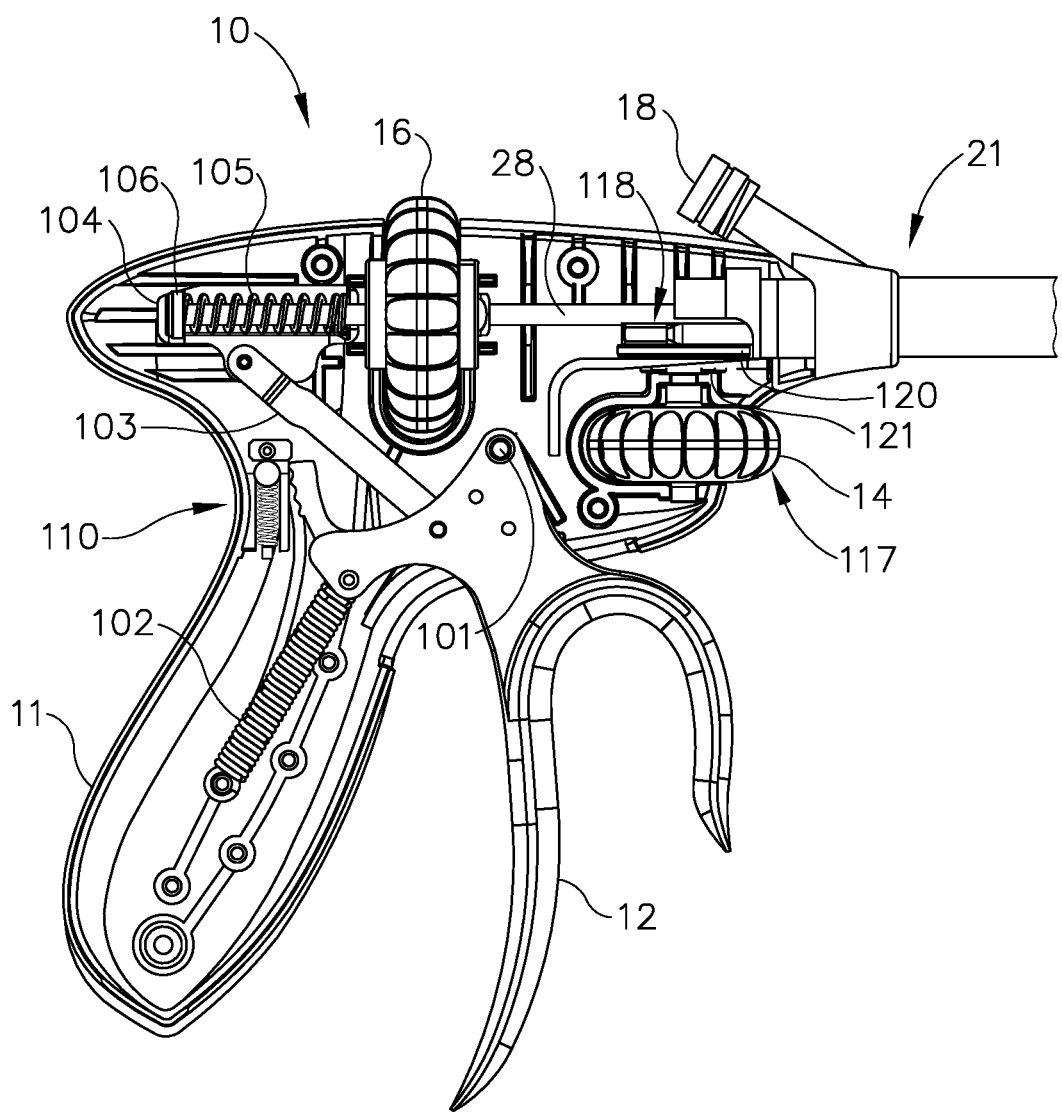
FIG. 3 depicts a side elevational view of the handle assembly of the instrument of FIG. 1, with a housing half removed to reveal internal components.

With respect to FIG. 1 and FIG. 3, articulation control assembly (117) includes rotary knob (14) and a joint drive assembly (118). Rotary knob (14) is operable to selectively articulate joint (23) via joint drive assembly (118). More particularly, rotary knob (14) rotates in a plane spaced below and generally parallel with shaft (20). Joint drive assembly (118) includes rods (27A, 27B) and a first exemplary disk (120). An axle (121) connects rotary knob (14) to disk (120) in housing (11) that also rotates in a plane generally parallel with the shaft (20). As shown in FIG. 4, disk (120) comprises first and second cam slots (122A, 122B), each having a length with angular and radial components. In this embodiment, the cam slots (122A, 122B) are two identical spirals offset 180 degrees from one another. Each cam slot (122A, 122B) has an angular span between about 220 degrees and about 300 degrees, with their angular spans overlapping one another. Cam slots (122A, 122B) also increase their distance from the center of disk (120) in the same angular direction. Each cam slot (122A, 122B) has a radial span of about 0.100 inches and about 0.155 inches. Of course, the configuration and dimensions of cam slots (122A, 122B) may alternatively differ from the foregoing.

Cam slot (122A) receives a cam follower (124A) on a distal half of disk (120), and cam slot (122B) receives a cam follower (124B) on the proximal half of disk (120). Followers (124A, 124B) extend downwardly and generally normal from the proximal ends of rods (27A, 27B), respectively. In this example, followers (124A, 124B) are medially offset from longitudinal axes of the respective drive rod (27A, 27B). Rods (27A, 27B) are constrained to slide axially, so counterclockwise rotation of disk (120) moves rod (27B) proximally and simultaneously moves rod (27A) distally to articulate joint (23) to the left of the longitudinal axis (LA) of shaft (20), as shown in the transition from FIG. 7A to FIG. 7B. Similarly, clockwise rotation of disk (120) moves rod (27B) distally and simultaneously moves rod (27A) proximally, thereby articulating joint (23) to the right of the longitudinal axis (LA) of shaft (20), as shown in the transition from FIG. 7A to FIG. 7C.

With respect to FIG. 4 and FIG. 7A, cam slots (122A, 122B) each define a tangent axis (126A, 126B) where cam slot (122A, 122B) is engaged by the respective cam followers (124A, 124B). The tangent axes (126A, 126B) may be substantially normal to the longitudinal axes of rods (27A, 27B) so axial push and pull loads on rods (27A, 27B) introduced by side loads on cartridge receiving assembly (50) will not cause disk (120) to rotate. Accordingly, joint (23) will remain locked at its articulated angle. Frictional interfaces, detents, and other locking features, such as those discussed below, may be added to further prevent unintentional articulation.

FIG. 5 illustrates an alternative example of an articulation control. A plurality of detents (125) are positioned along cam slots (122A, 122B). In addition to preventing unintentional articulation, detents (125) may provide feedback to the surgeon indicating various angular positions of needle applier cartridge (30) relative shaft (20). Detents (125) may be indexed to correspond to one or more predetermined articulation angles, such as 0 degrees, 15 degrees, 45 degrees, and the like; or detents (125) may be equally distributed along cam slots (122A, 122B). Larger detents (127) may be located at the ends of the cam slots (122A, 122B).

Detents (125) open to the top surface of a second exemplary disk (120'), but only partially extend into cam slots (122A, 122B). As shown in FIG. 6, follower (124) extends downwardly from articulation rod (27). Follower (124) includes a straight portion (124C) that closely fits in cam slots (122A, 122B) and a radius portion (124D) dimensioned to be received by detents (125). As disk (120') rotates, radius portion (124D) will raise and lower into detents (125) but the straight portion (124C) will follow and remain engaged in the cam slots (122A, B). In some versions, rod (27) will be biased downwardly toward disk (120') to provide a tactile and/or audible "click" as radius portion (124D) engages detents (125).

Further details, explanations, examples, and alternative embodiments of surgical suturing devices and subcomponents of the foregoing are disclosed in U.S. Pat. No. 9,357,998, entitled "Circular Needle Applier with Articulating and Rotating Shaft," issued Jun. 7, 2016, the disclosure of which is incorporated by reference herein; U.S. Pat. No. 9,474,522, entitled "Jawed Receiver for Needle Cartridge," issued Oct. 25, 2016, the disclosure of which is incorporated by reference herein; U.S. Pat. No. 9,375,212, entitled "Circular Needle Applier with Cleats," issued Jun. 28, 2016, the disclosure of which is incorporated by reference herein; and U.S. Pat. No. 9,888,914, entitled "Suturing Instrument with Motorized Needle Drive," issued Feb. 13, 2018, the disclosure of which is incorporated by reference herein. It should be understood that such details, explanations, examples, and alternative embodiments may be readily applied to the above-described instrument (2) and subcomponents thereof.

II. Exemplary Handle Assembly with Locking Articulation Joint

In some instances, it may be desirable to provide feedback to the operator regarding the position of cartridge receiving assembly (50) relative to a remainder of surgical suturing instrument (2), such as the relative angular position of cartridge receiving assembly (50). For example, tactile feedback may be provided to the operator by a position indicator (212, 218, 242, 252, 262, 282) to indicate that cartridge receive assembly (50) is in a straight, longitudinal alignment with the longitudinal axis (LA) of shaft (20), also referred to herein as a "center position." It may be further desirable to selectively lock articulation joint (23) in one of a plurality of positions in a way that secures cartridge receiving assembly (50) relative to a remainder of shaft assembly (19) and inhibits inadvertent movement of cartridge receiving assembly (50) at articulation joint (23) during use. For instance, in the event that the operator inadvertently bumps the cartridge receiving assembly (50) against another object, such as patient tissue or other surgical equipment, cartridge receiving assembly (50) will retain its desirable position (i.e., angular orientation) articulation joint (23). In some examples, surgical suturing instrument (2) has a joint stabilizer (316, 416) operatively connected to cartridge receiving assembly (50) for retaining such a desirable position. Additionally or alternatively, another joint stabilizer (516) operatively connects to articulation joint (23) to automatically lock and unlock in one of the plurality of positions upon selective movement of rotary knob (14) for greater simplicity during a surgical procedure.

Various examples of how surgical suturing instrument (2) may be reconfigured to incorporate various position indicators and/or joint stabilizers (212, 218, 242, 252, 262, 282, 316, 416, 516) will be described in greater detail below with respect to surgical instrument (2) discussed above; while other examples will be apparent to those of ordinary skill in the art according to the teachings herein. Such position indicators and/or joint stabilizers (212, 218, 242, 252, 262, 282, 316, 416, 516) may be used alone or in any combination in any alternative surgical suturing instrument. It should be understood that the examples described below may function substantially similar to instrument (2) described above. In particular, instrument (202) described below may be used to suture tissue. To this end, like numbers referenced below indicate like features discussed above in greater detail.

While the below descriptions refer to right or rightward (i.e., clockwise) rotation and left or leftward (i.e., counterclockwise) rotation, it will be appreciated that either leftward or rightward rotation is contemplated for positioning and locking articulation joint (23) of FIG. 1 in any case. It will be appreciated that the above description will effectively occur in the opposite directions to those discussed below. Versions with reusable components are intended to be cleaned, sterilized, and reused for multiple surgical procedures, and may include a flush port (not shown) to facilitate cleaning. In some such versions, the preferable life cycle of a reusable instrument may be at least 50 operations, more particularly at least 150 operations, or more particularly at least 200 operations. Reusable components may be built using materials that can withstand autoclave sterilization temperatures of at least 135 degrees Celsius, although low temperature materials can also be used with low temperature sterilization techniques known in the art.

A. Surgical Suturing Instrument with a Position Indicator

FIGS. 8-12C show a second exemplary rotary knob (210) with a first example of a knob position indicator (212) as well as a third exemplary disk (214) for use with remaining portions of articulation control assembly (117) discussed above in greater detail. Knob position indicator (212) includes a position projection (216) that rotates about an axis (KA) and operatively keys to the angular position of cartridge receiving assembly (50) (see FIG. 7A) relative to shaft (20) (see FIG. 7A) to indicate such position to the operator. The particular position of position projection (216) about axis (KA) indicates a predetermined angular position of cartridge receiving assembly (50) (see FIG. 7A). Position projection (216) is configured to be gripped, manipulated, and visualized to tactilely and visually provide a position feedback regarding the predetermined angular position of cartridge receiving assembly (50) (see FIG. 7A) to the operator during use. Furthermore, in the present example, knob position indicator (212) is paired with a detent position indicator (218) having a detent abutment (220) and corresponding detent notch (222). Detent abutment (220) is configured to engage detent notch (222) to tactilely and/or audibly generate additional position feedback regarding the predetermined angular position of cartridge receiving assembly (50) (see FIG. 7A) to the operator during use. While the present example includes both knob position indicator (212) in conjunction with detent position indicator (218), an alternative position indicator may include one or more of such indicators. The invention is thus not intended to be unnecessarily limited to the exemplary pairing of knob and detent position indicators (212, 218) shown in the present example.

Figure 8:
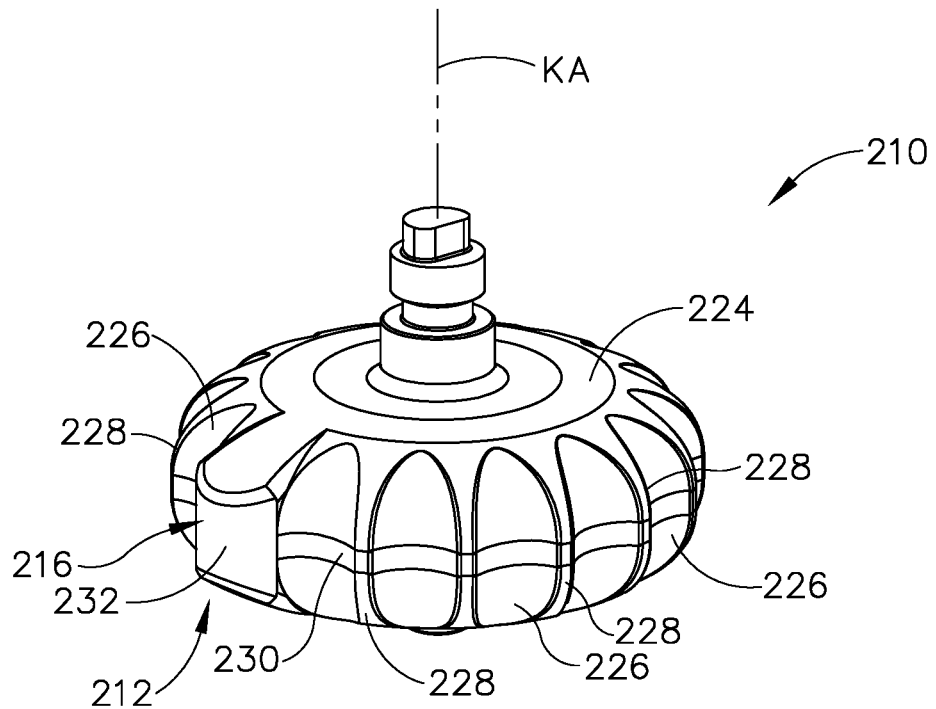
FIG. 8 depicts a perspective view of a second exemplary rotary knob having a first example of a knob position indicator for use with the articulation control assembly of FIG. 4.
Figure 9:
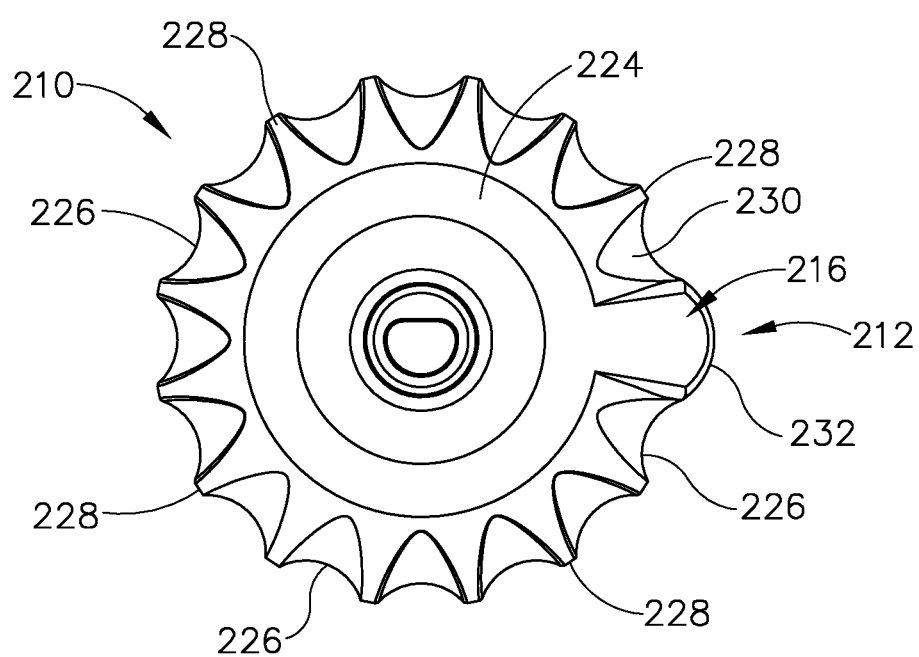
FIG. 9 depicts a top plan view of the rotary knob with the knob position indicator of FIG. 8.

With respect to FIGS. 8-9, rotary knob (210) has an annular wheel body (224) and a plurality of concave channels (226), which taper together upward and downward toward axis (KA). Concave channels (226) thereby define a lip (228) between each pair of concave channels (226) such that concave channels (226) and lips (228) collectively provide an outer annular surface (230). Each concave channel (226) extends radially outward from axis (KA) a channel radius, whereas lip (228) extends radially outward further from axis (KA) a first lip radius. Concave channels (226) and lips (228) thereby define a repeating pattern about outer annular surface (230) configured to be gripped and manipulated by the operator.

Position projection (216) extends radially outward from annular wheel body (224) and tapers together upward and downward toward axis (KA). Position projection (216) has a convex surface (232) that more particularly extends radially outward from axis (KA) a first projection radius and connects laterally to adjacent concave channels (226) on each side thereof. Position projection (216) is positioned between a pair of concave channels (226) with the annular, repeating pattern extending about the remainder of outer annular surface (230). First projection radius of convex surface (232) is larger than first lip radius and, indeed, a majority of convex surface (232) extends beyond first lip radius. Position projection (216) is thereby distinct from the repeating pattern about outer annular surface (230) to provide visual and tactile position feedback.

Figure 10:
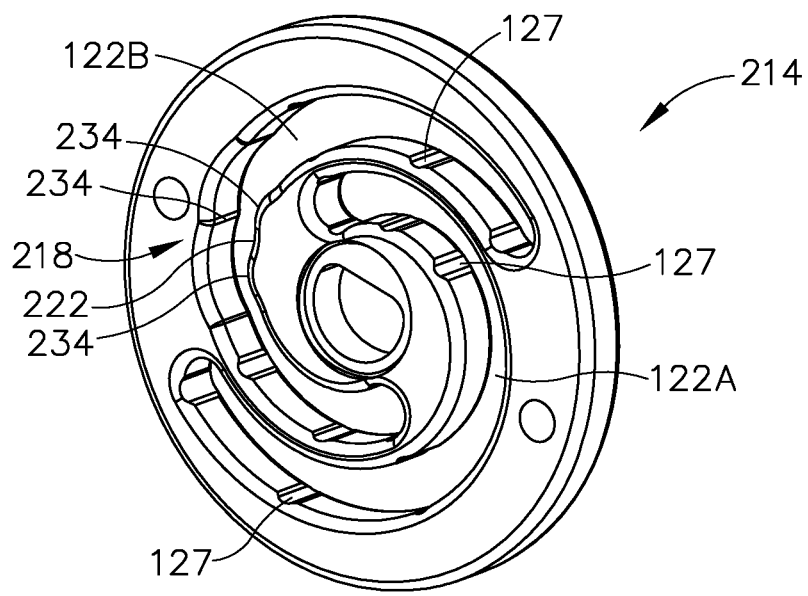
FIG. 10 depicts a perspective view of a third exemplary disk having a first example of a detent position indicator for use with the articulation control assembly of FIG. 4.
Figure 11:
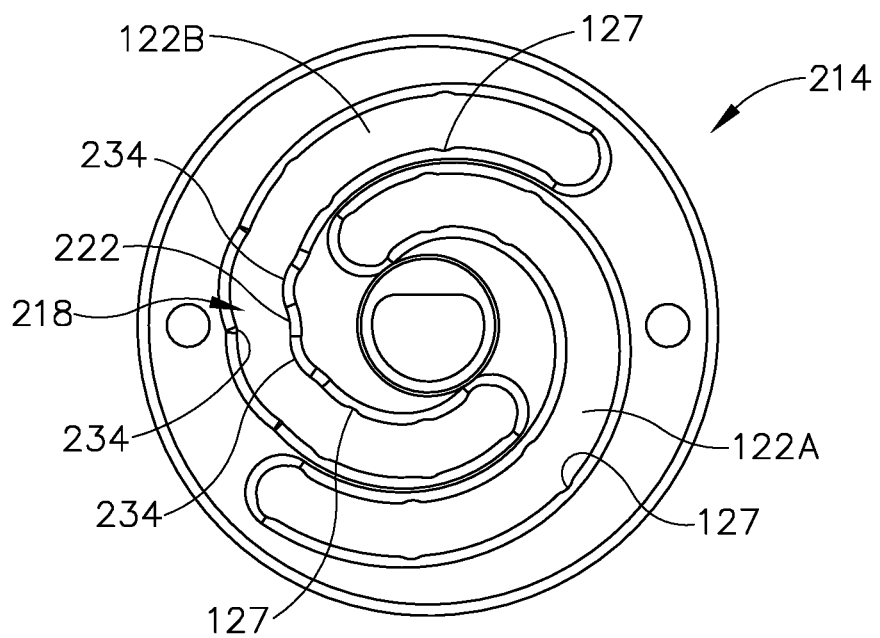
FIG. 11 depicts a top plan view of the disk with the detent position indicator of FIG. 10.

FIGS. 10-11 show disk (214) with cam slots (122A, 122B) and detent notch (222) of detent position indicator (218) positioned within slot (122A). As discussed above, each cam slot (122A, 122B) has an angular span between about 220 degrees and about 300 degrees, with their angular spans overlapping one another. Cam slots (122A, 122B) also increase their distance from the center of disk (120) in the same angular direction. Thereby, cam slots (122A, 122B) direct movement of cam followers (124A, 124B) (see FIG. 12A). In the present example, detent notch (222) is positioned within cam slot (122B) with various follower crowns (234) extending into cam slot (122B) about detent notch (222). More particularly, detent notch (222) is further defined and positioned between a pair of follower crowns (234) and opposite from another follower crown (234). With respect to FIG. 11 and FIG. 12A, follower crowns (234) urge detent abutments (220), which are positioned on cam followers (124B), to further enhance tactile and/or audible feedback generated by detent position indicator (218).

Figure 12A:
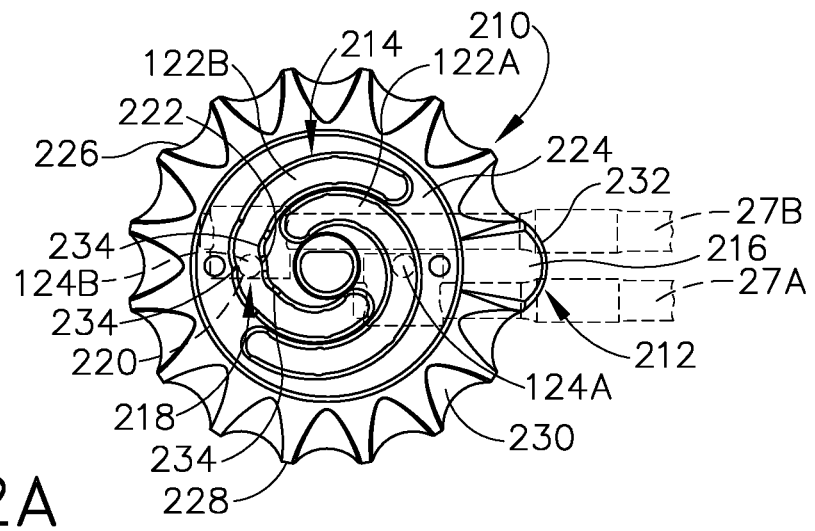
FIG. 12A depicts a top plan view of the rotary knob with the knob position indicator of FIG. 8 and the disk with the detent position indicator of FIG. 10 in a center position with the articulation control assembly of FIG. 4, which is hidden for clarity.
Figure 12B:
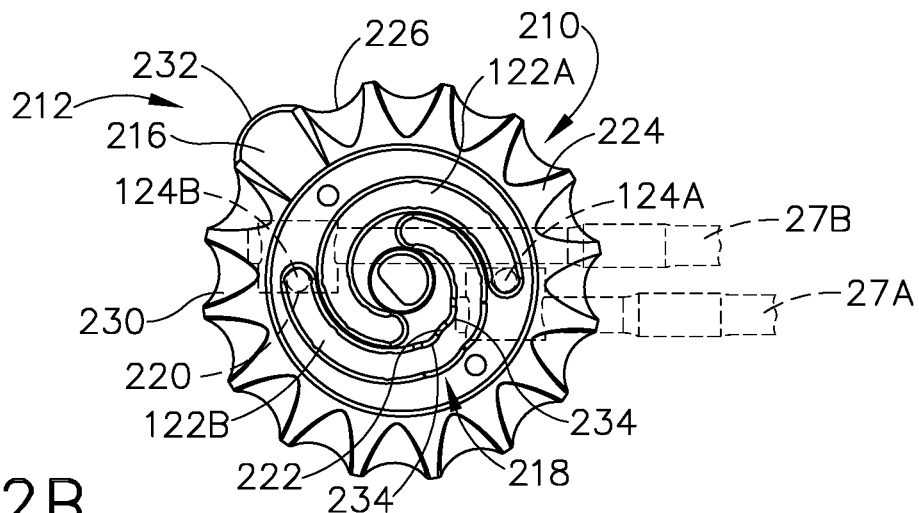
FIG. 12B depicts the top plan view of the rotary knob and the disk similar to FIG. 12A, but showing the knob position indicator and the detent position indicator in a left position.
Figure 12C:
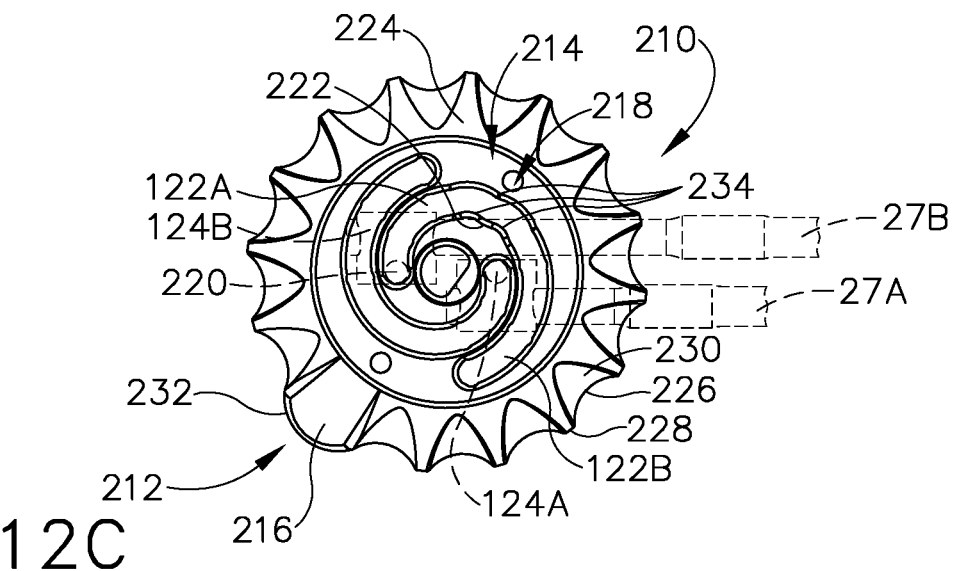
FIG. 12C depicts the top plan view of the rotary knob and the disk similar to FIG. 12B, but showing the knob position indicator and the detent position indicator in a right position.
Figure 20:
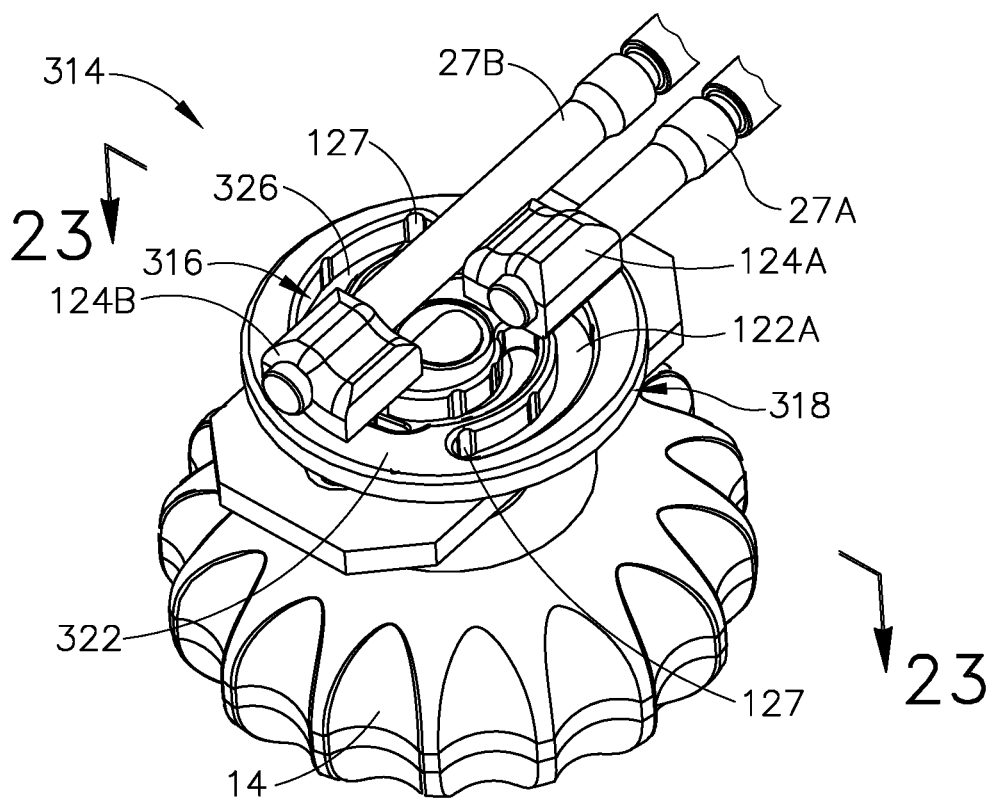
FIG. 20 depicts a perspective view of a second example of an articulation control assembly including a fifth exemplary disk with an inner drive stabilization indicator.

To this end, FIGS. 12A-12C show knob position indicator (212) and detent position indicator (218) providing visual, tactile, and/or audible feedback corresponding to predetermined angular positions of cartridge receiving assembly (50) (see FIG. 7A). In the present example of knob position indicator (212), FIG. 12A depicts position projection (216) in a center position, which is operatively keyed with cartridge receiving assembly (50) in longitudinal alignment with axis (LA) as shown in FIG. 7A. In contrast, FIG. 12B depicts position projection (216) in a left position, which is operatively keyed with cartridge receiving assembly (50) in a leftward alignment relative to axis (LA) as shown in FIG. 7B. FIG. 12C depicts position projection (216) in a right position, which is operatively keyed with cartridge receiving assembly (50) in a rightward alignment relative to axis (LA) as shown in FIG. 7C.

With respect to detent position indicator (218), detent abutment (220) on cam follower (124B) is seated within detent notch (222) in the center position as shown in FIG. 12A. Thus, directing rotation of rotary knob (210) from the center toward the left or right positions shown in FIGS. 12B-12C or from the left or right positions to the center position generates a tactile resistance as detent abutment (220) engages follower crowns (234) and/or settles into detent notch (222). In the present example, the tactile and/or audible feedback communicated to the operator as detent abutment (220) engages follower crowns (234) and detent notch (222) indicates that rotary knob (210) is in the center position with cartridge receiving assembly (50) in the predetermined angular position of FIG. 7A.

By way of further examples, FIGS. 13-14 show a third exemplary rotary knob (240) having a second knob position indicator (242) and annular wheel body (224). A position projection (244) of knob position indicator (242) rotates about axis (KA) and operatively keys to the angular position of cartridge receiving assembly (50) (see FIG. 7A) relative to shaft (20) (see FIG. 7A). Concave channels (226), lips (228), and position projection (244) collectively provide an outer annular surface (246). Each concave channel (226) extends radially outward from axis (KA) a channel radius, whereas lip (228) extends radially outward further from axis (KA) a first lip radius. Concave channels (226) and lips (228) thereby define the repeating pattern about outer annular surface (246) configured to be gripped and manipulated by the operator.

Position projection (244) extends radially outward from annular wheel body (224) and tapers together upward and downward toward axis (KA). Position projection (244) has a convex surface (248) that more particularly extends radially outward from axis (KA) a second projection radius. Position projection (244) is positioned between a pair of concave channels (226) with the annular, repeating pattern extending about the remainder of outer annular surface (246). Second projection radius of convex surface (248) is generally equivalent to first lip radius. Position projection (244) is thereby distinct from the repeating pattern about outer annular surface (246) to provide visual and tactile position feedback.

FIGS. 15-16 show a fourth exemplary rotary knob (250) having a third knob position indicator (252) and annular wheel body (224). A position recess (254) of knob position indicator (252) rotates about axis (KA) and operatively keys to the angular position of cartridge receiving assembly (50) (see FIG. 7A) relative to shaft (20) (see FIG. 7A). Concave channels (226), lips (228), and position recess (254) collectively provide an outer annular surface (256). Each concave channel (226) extends radially outward from axis (KA) a channel radius, whereas lip (228) extends radially outward further from axis (KA) a first lip radius. Concave channels (226) and lips (228) thereby define the repeating pattern about outer annular surface (256) configured to be gripped and manipulated by the operator.

Position recess (254) extends radially inward through annular wheel body (224) toward axis (KA) and tapers together upward and downward toward axis (KA). Position recess (254) has a concave surface (258) that more particularly extends radially inward to axis (KA) a third projection radius. Position recess (254) is positioned between a pair of enlarged lips (259) with the annular, repeating pattern extending about the remainder of outer annular surface (256). Third projection radius of concave surface (258) is less than first lip radius and, indeed, even less than channel radius. Position recess (254) is thereby distinct from the repeating pattern about outer annular surface (256) to provide visual and tactile position feedback.

FIGS. 17-18 show a fifth exemplary rotary knob (260) having a third knob position indicator (262) and annular wheel body (224). A position projection (264) of knob position indicator (262) rotates about axis (KA) and operatively keys to the angular position of cartridge receiving assembly (50) (see FIG. 7A) relative to shaft (20) (see FIG. 7A). Concave channels (226), lips (228), and position projection (264) collectively provide an outer annular surface (266). Each concave channel (226) extends radially outward from axis (KA) a channel radius, whereas lip (228) extends radially outward further from axis (KA) a first lip radius. Concave channels (226) and lips (228) thereby define the repeating pattern about outer annular surface (266) configured to be gripped and manipulated by the operator.

Position projection (264) extends radially outward from annular wheel body (224) and tapers together upward and downward toward axis (KA). Position projection (264) has a convex surface (268) that more particularly extends radially outward from axis (KA) a fourth projection radius. Position projection (264) is positioned between a pair of enlarged concave channels (269) with the annular, repeating pattern extending about the remainder of outer annular surface (266). Fourth projection radius of convex surface (268) is generally equivalent to first lip radius. Position projection (264) is thereby distinct from the repeating pattern about outer annular surface (266) to provide visual and tactile position feedback.

FIG. 19 shows a fourth exemplary disk (280) having a second detent position indicator (282). Detent position indicator (282) is generally similar to detent position indicator (218) discussed above, but includes an additional detent notch (222) and follower crowns (234) positioned within cam slot (122A) configured to releasably capture cam follower (124A), which has an additional detent abutment (220). Such additional detent notch (222) detent abutment (220) that respectively correspond to cam slot (122A) and cam follower (124A) are similarly operatively keyed to the center position and, in this respect, operate as those discussed above with respect to FIGS. 12A-12C to further enhance the generation of tactile feedback.

As discussed above, knob position indicators (212, 242, 252, 262) and detent position indicators (218, 282) simultaneously provide visual and tactile feedback to indicate the center position to the operator. In other examples, knob position indicators (212, 242, 252, 262) and detent position indicators (218, 282) may alternatively configured to provide different and distinct positions. The invention is thus not intended to be unnecessarily limited to simultaneously indicating such predetermined positions. Furthermore, detent position indicators (218, 282) may be similarly configured as discussed above to provide additional stability to articulation joint (23) (see FIG. 7A) as a joint stabilizer, details of which will be provided below in various examples. Such detent position indicators (218, 282) may thus function as joint stabilizers, and are not intended to be unnecessarily limited to only indicating one or more positions to the operator.

B. Second Example of an Articulation Control Assembly with an Inner Drive Stabilization Indicator FIGS. 20-23 show a second example of an articulation control assembly (314) for use in place of articulation control assembly (117) (see FIG. 3) of surgical instrument (2) (see FIG. 1) discussed above in greater detail. Articulation control assembly (314) includes an inner drive stabilization indicator (316) configured to arrest actuation of a joint drive assembly (318) and thereby inhibit articulation of cartridge receiving assembly (50) (see FIG. 7A) relative to shaft (20) (see FIG. 7A). More particularly, with respect to FIGS. 20-21, inner drive stabilization indicator (316) has a biasing detent (320) cooperatively engaged with a fifth exemplary disk (322) and cam follower (124B), which is connected to rod (27B). Biasing detent (320) resiliently and releasably captures movement of disk (322) and, in turn, rod (27B) to thereby stabilize cartridge receiving assembly (50) (see FIG. 7A) relative to shaft (20) (see FIG. 7A).

Figure 21:
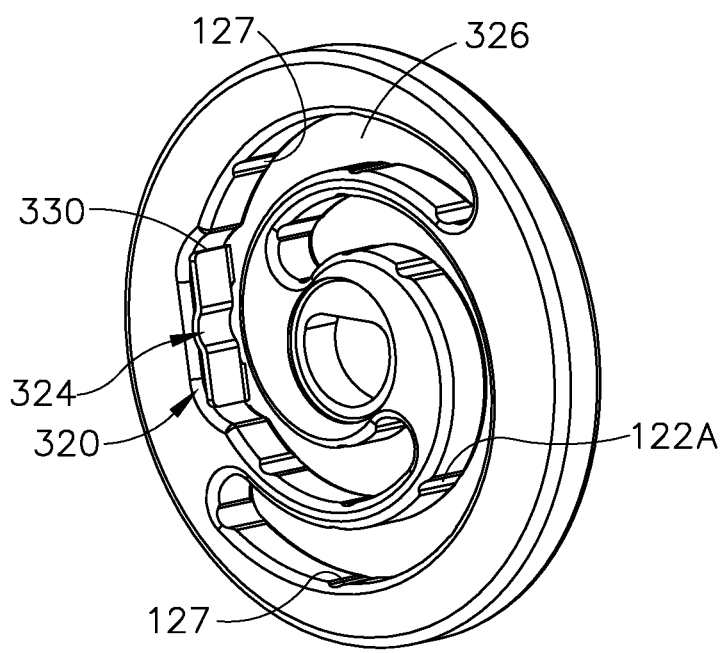
FIG. 21 depicts a lower perspective view of the disk and the inner drive stabilization indicator of FIG. 20.
Figure 22:
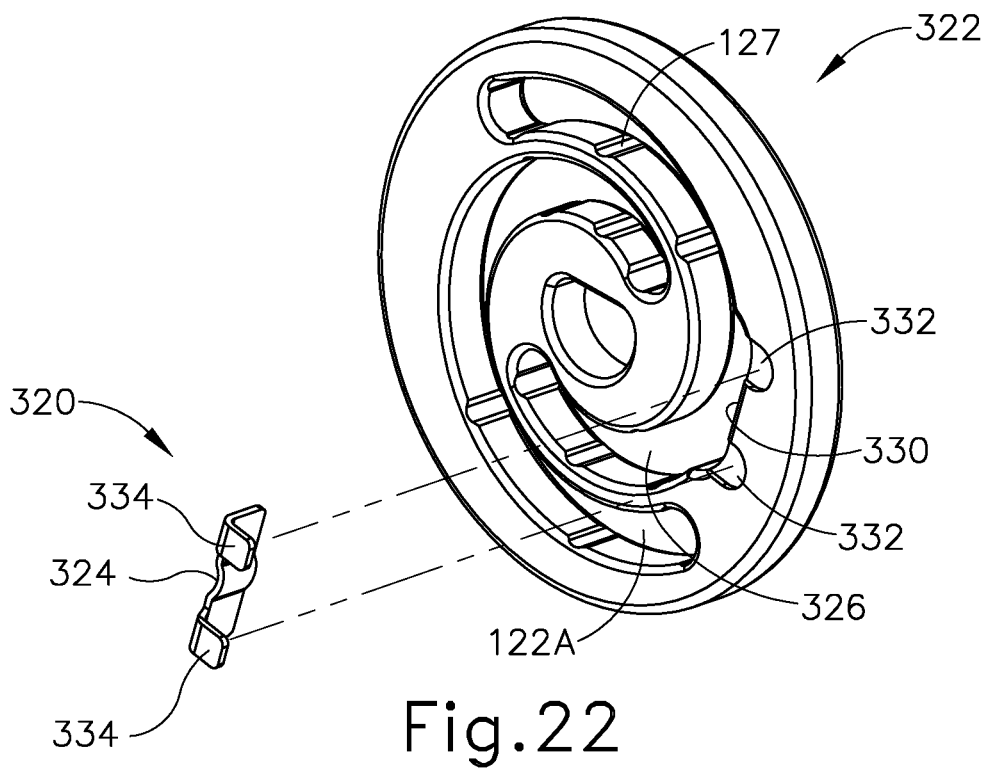
FIG. 22 depicts a partially exploded upper perspective view of the disk and the inner drive stabilization indicator of FIG. 20.
Figure 23:
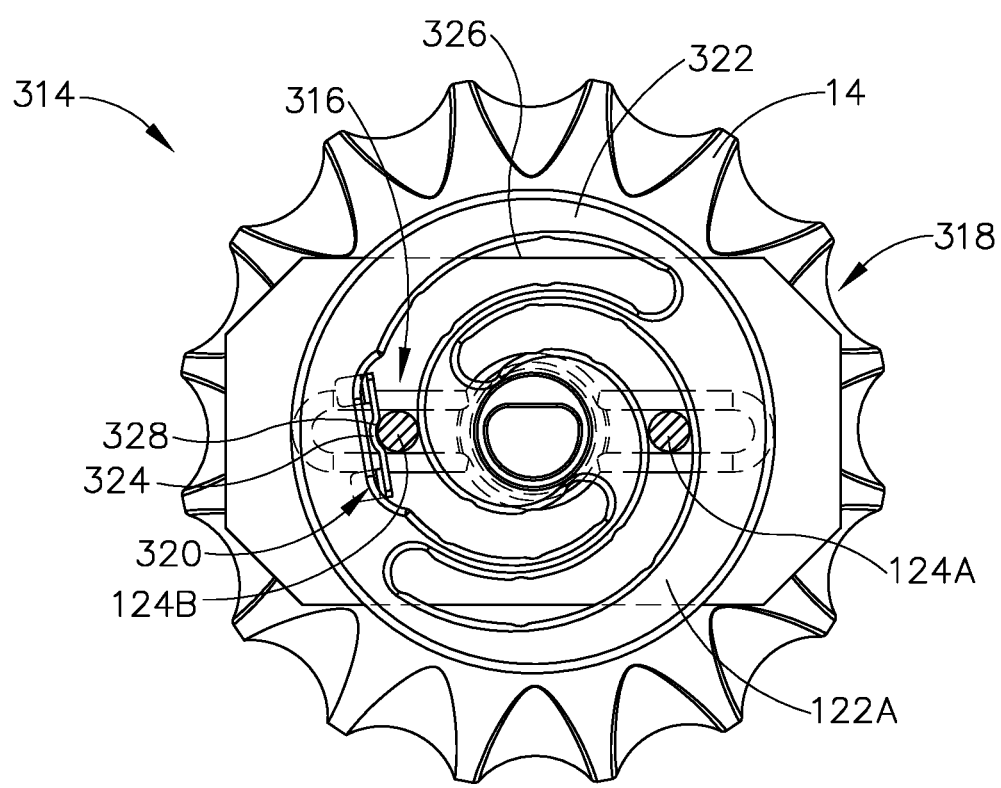
FIG. 23 depicts a cross-sectional view of the articulation control assembly of FIG. 21 taken along section line 23-23 of FIG. 20.
Figure 24:
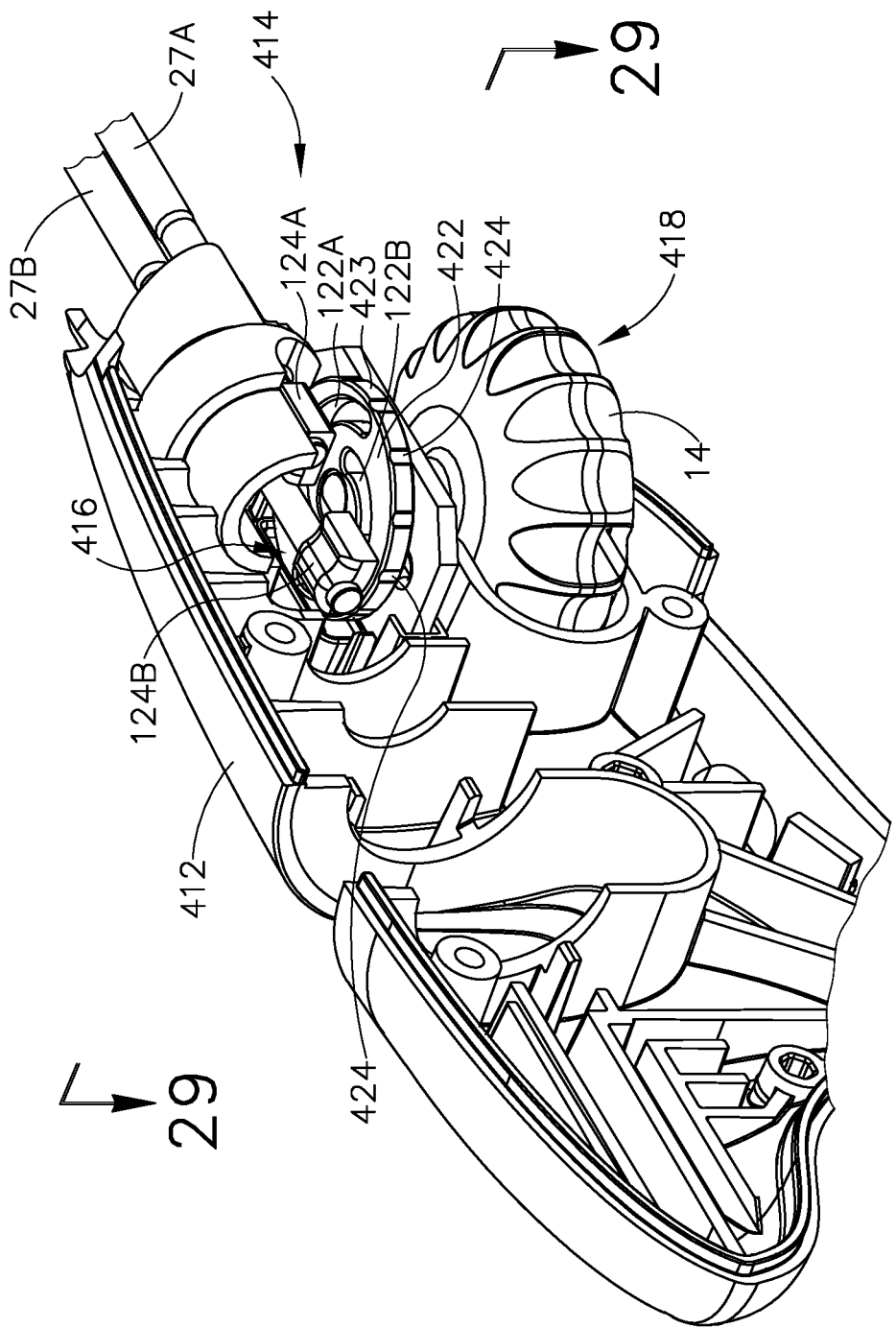
FIG. 24 depicts a perspective view of a third example of an articulation control assembly and a sixth exemplary disk with an outer drive stabilization indicator positioned within a portion of a housing.
Figure 25:
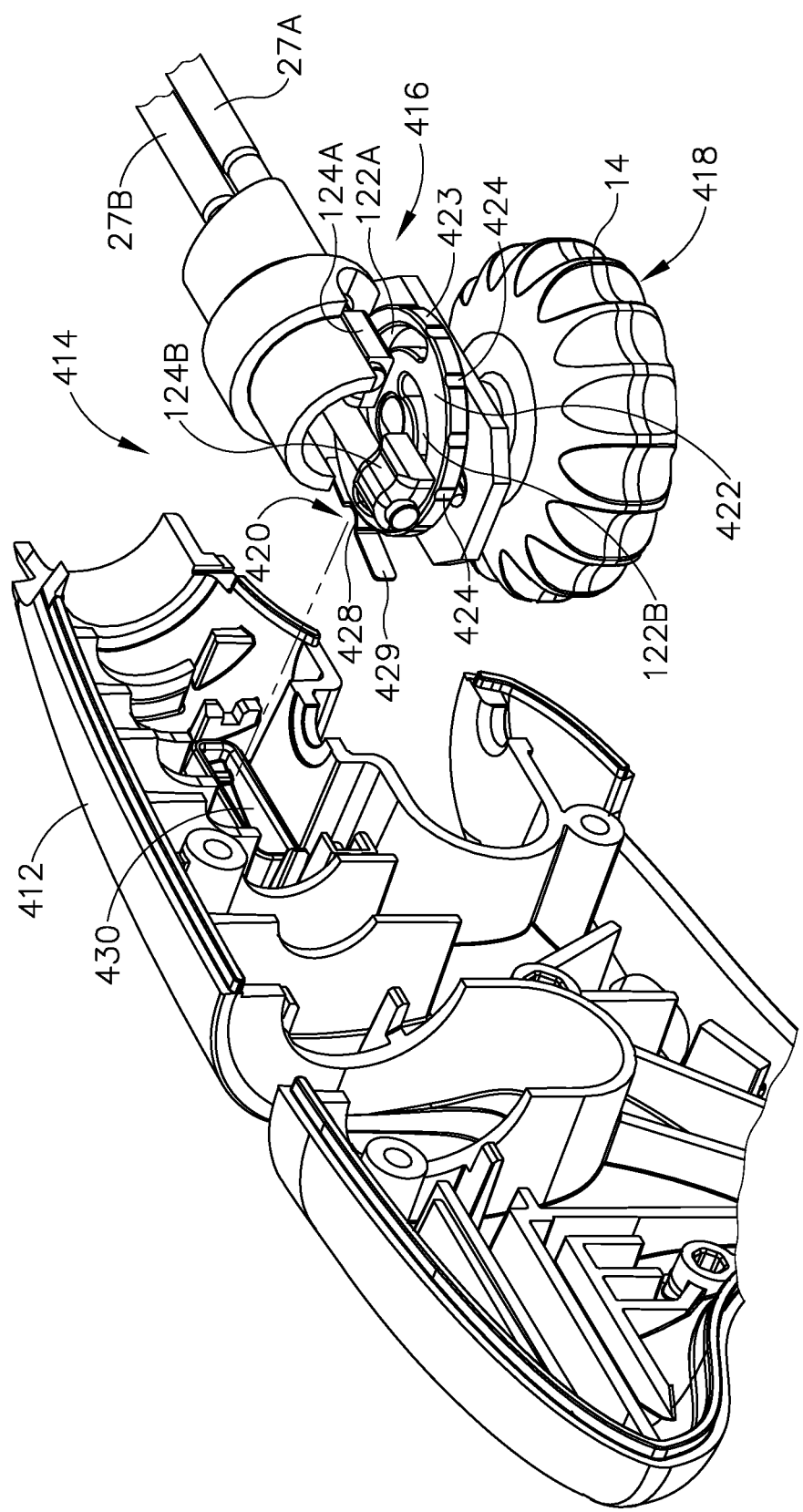
FIG. 25 depicts a partially exploded perspective of the articulation control assembly and the disk with the outer drive stabilization indicator removed from the portion of the housing of FIG. 24.

In the present example, biasing detent (320) is secured to disk (322) as shown in FIGS. 21-22 such that a resilient detent notch (324) is positioned within a cam slot (326) to engage a detent abutment (328) on cam follower (124B) (see FIG. 23). A clearance recess (330) extends through a portion of disk (322) adjacent to cam slot (326) to receive biasing detent (320) therein. Clearance recess (330) provides ample space for both resilient deformation of detent notch (324) as well as cutouts (332) configured to receive mounting tabs (334) extending from biasing detent (320). Mounting tabs (334) may be pressed with adhesive into cutouts (332) for securement or any other known method for securing such biasing detent (320) to disk (322). The invention is thus not intended to be limited to the particular disk (322) and biasing detent (320) as shown and described herein.

With respect to FIG. 23, rotating rotary knob (14) similarly rotates disk (322) and guides movement of cam followers (124A, 124B) along cam slots (122A, 326) as discussed above. Detent notch (324) and detent abutment (328) of the present example are collectively positioned to correspond to the center position of knob (14) and alignment of cartridge receiving assembly (50) (see FIG. 7A) along longitudinal axis (LA). Thus, detent notch (324) resiliently and releasably captures detent abutment (328) to arrest actuation of disk (322) and, in turn, cartridge receiving assembly (50) (see FIG. 7A). Furthermore, in the present example, biasing detent (320) generates tactile and/or audible feedback to simultaneously indicate to the operator that knob (14) is in the center position as discussed above with respect to various detent position indicators (218, 282). Inner drive stabilization indicator (316) is thereby configured to indicate one or more predetermined positions to the operator during use. Inner drive stabilization indicator (316) is thus not intended to be unnecessarily limited to only one of stabilization or positioning.

C. Third Example of an Articulation Control Assembly with an Outer Drive Stabilization Indicator FIGS. 24-30B show a portion of a housing (412) receiving a fourth example of an articulation control assembly (414) for use in place of articulation control assembly (117) (see FIG. 3) of surgical instrument (2) (see FIG. 1) discussed above in greater detail. Articulation control assembly (414) includes an outer drive stabilization indicator (416) configured to arrest actuation of a joint drive assembly (418) and thereby inhibit articulation of cartridge receiving assembly (50) (see FIG. 7A) relative to shaft (20) (see FIG. 7A). More particularly, with respect to FIGS. 24-25, outer drive stabilization indicator (416) has a biasing detent (420) cooperatively engaged with a sixth exemplary disk (422). Biasing detent (420) resiliently and releasably captures movement of disk (422) and, in turn, rod (27B) to thereby stabilize cartridge receiving assembly (50) (see FIG. 7A) relative to shaft (20) (see FIG. 7A).

Figure 26:
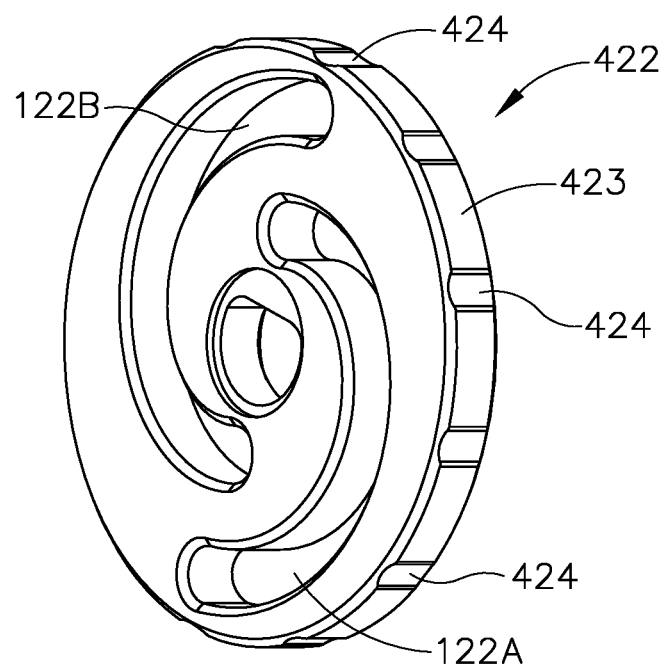
FIG. 26 depicts a perspective view of the disk of FIG. 24.
Figure 27:
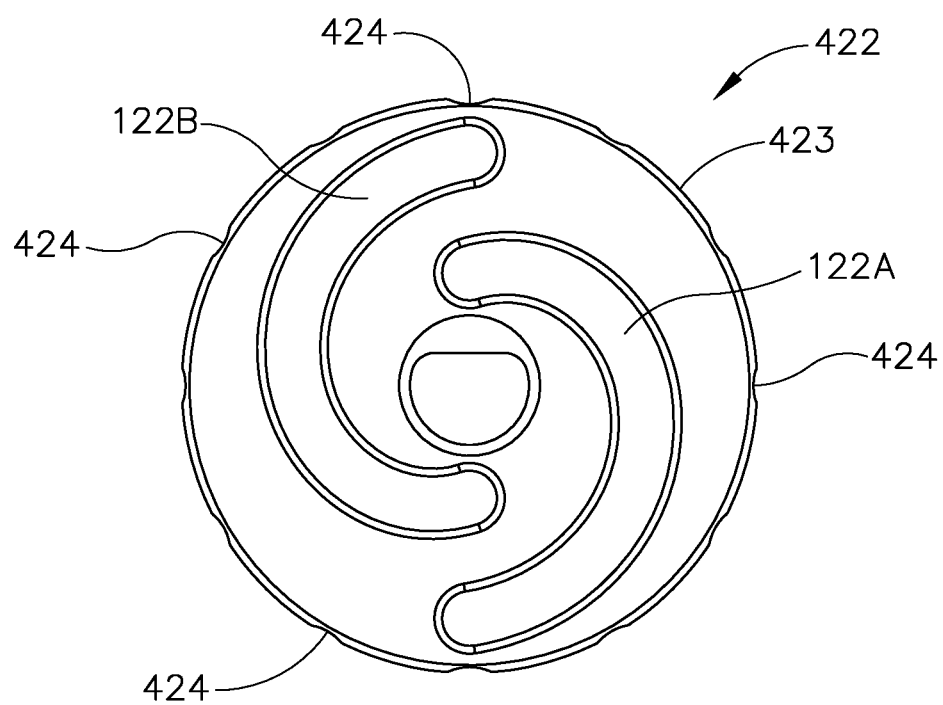
FIG. 27 depicts a top plan view of the disk of FIG. 24.
Figure 28:
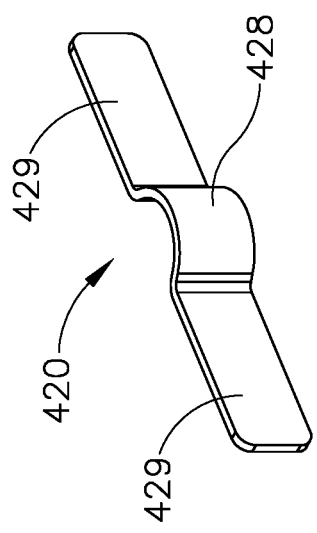
FIG. 28 depicts a perspective view of a biasing detent of the outer drive stabilization indicator of FIG. 24.
Figure 29:
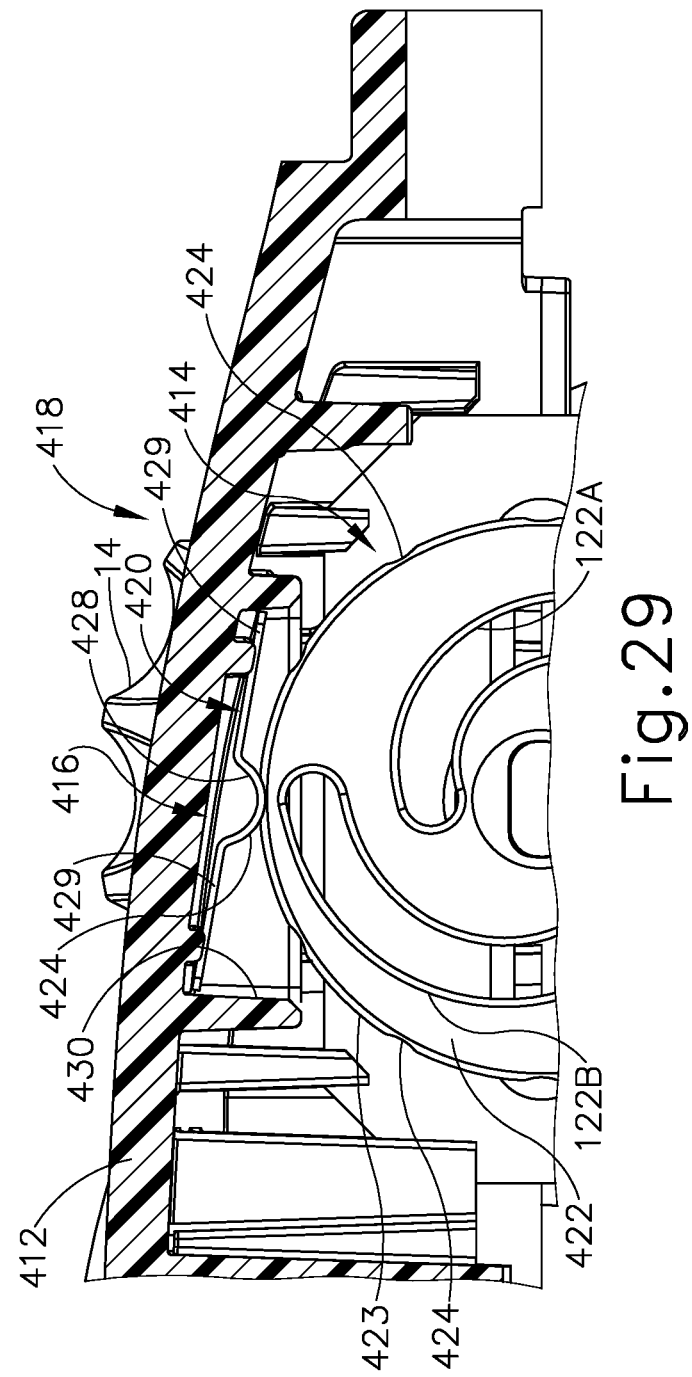
FIG. 29 depicts a cross-sectional view of the articulation control assembly of FIG. 24 taken along section line 29-29 of FIG. 24 and showing the biasing detent seated against the disk.

As shown in FIGS. 26-27, disk (422) has cam slots (122A, 122B) and an outer peripheral surface (423) with a plurality of detent notches (424) extending therethrough. Detent notches (424) are angularly positioned about outer peripheral surface (428) and correspond to predetermined positions of knob (14). In the present example, outer peripheral surface includes twelve detent notches positioned equiangularly about disk (422), 30 degrees apart from each other. Biasing detent (420) has a resilient detent abutment (428) extending outward from a pair of mounting legs (429) as shown in FIGS. 28-29. Biasing detent (420) is secured within housing (412) in a hollow (430) and positioned relative to disk (422) to resiliently engage outer peripheral surface (423). Mounting legs (334) may be pressed with adhesive into hollow (430) for securement or any other known method for securing such biasing detent (420) to housing (412). In one example, housing (412) includes a pair of hollows (430) respectively receiving a pair of biasing detents (420) on opposing sides of housing (412) Such pair of biasing detents (420) may provide additional engagement with disk (422). In this respect, the invention is not intended to be unnecessarily limited to one such biasing detent (420), and it will be appreciated that additional biasing detents (420) may be so used.

Figure 30A:
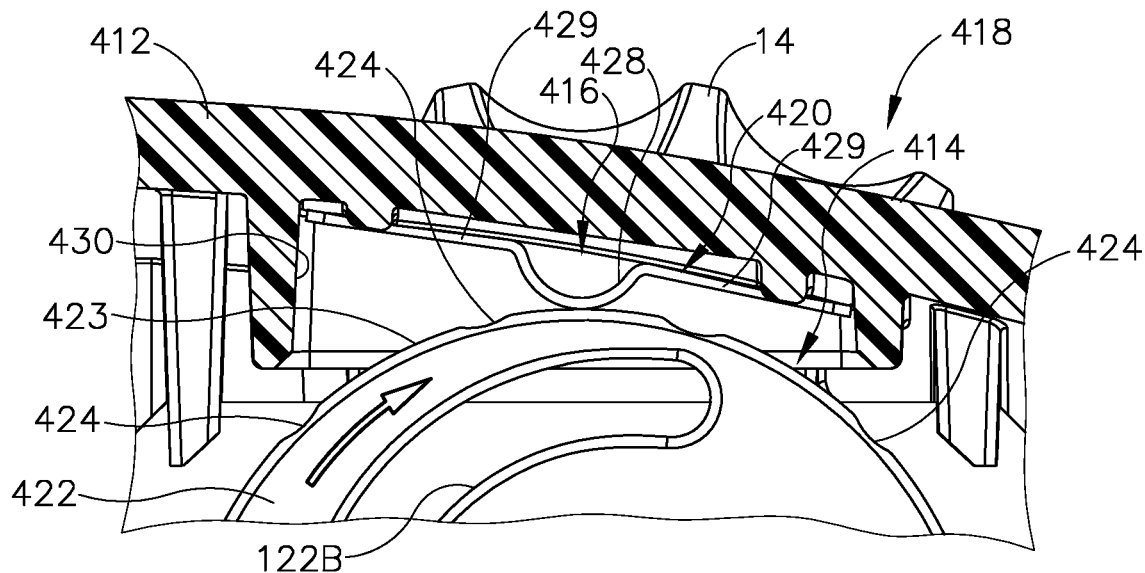
FIG. 30A depicts an enlarged cross-sectional view of the articulation control assembly similar to FIG. 29, but showing the biasing detent unseated and resiliently urged outward in engagement with the disk.
Figure 30B:
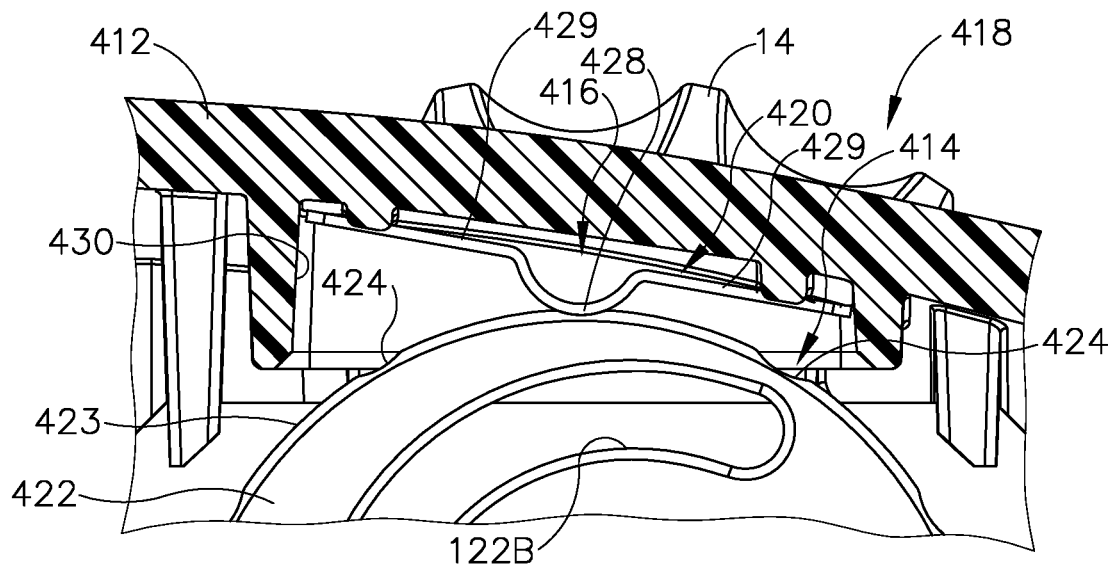
FIG. 30B depicts the enlarged cross-sectional view of the articulation control assembly and the disk with the outer drive stabilization indicator similar to FIG. 30A, but showing the biasing detent reseated against the disk.
Figure 31:
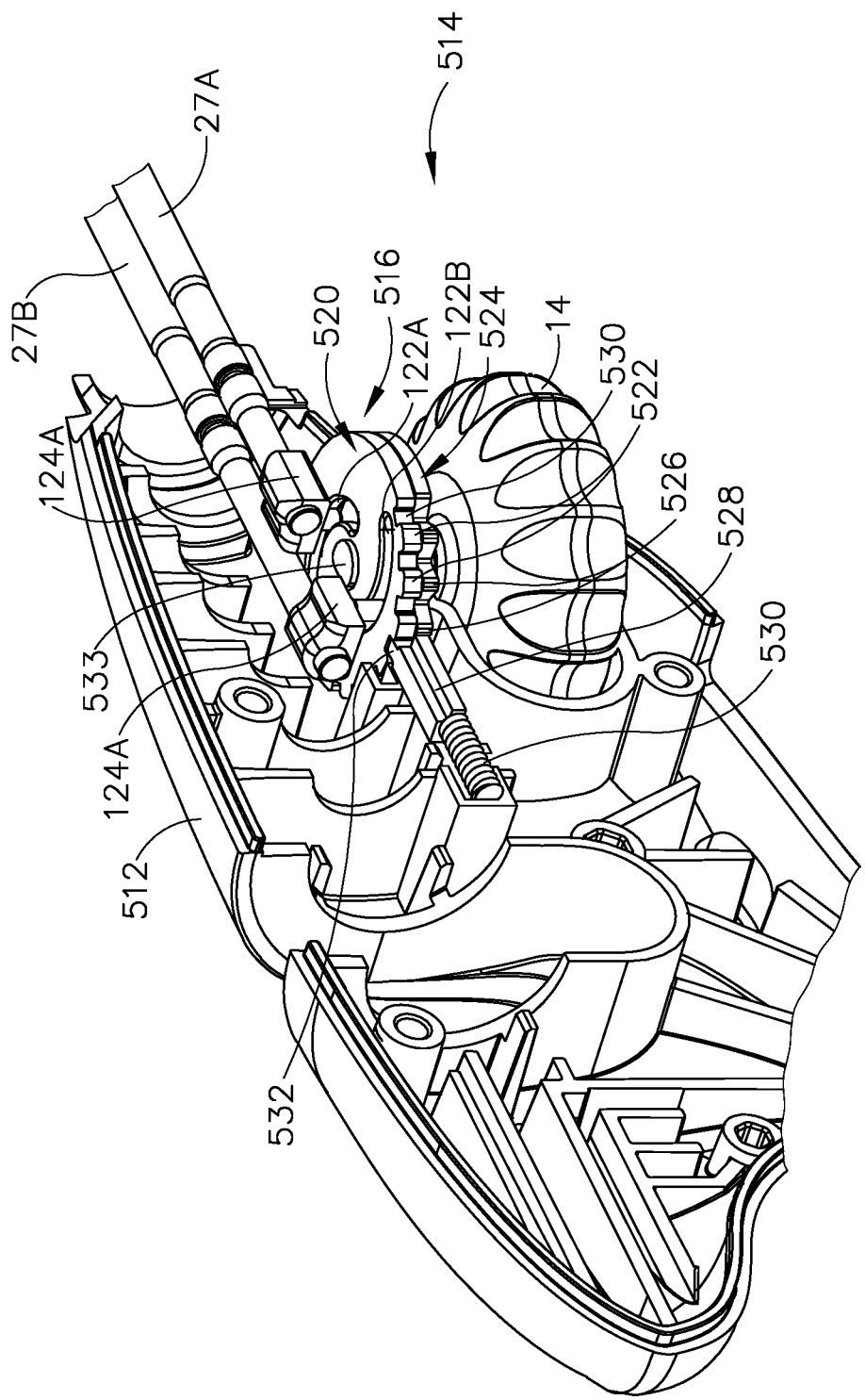
FIG. 31 depicts a perspective view of a fourth example of an articulation control assembly including a joint stabilization drive assembly positioned within a portion of a housing.
Figure 32:
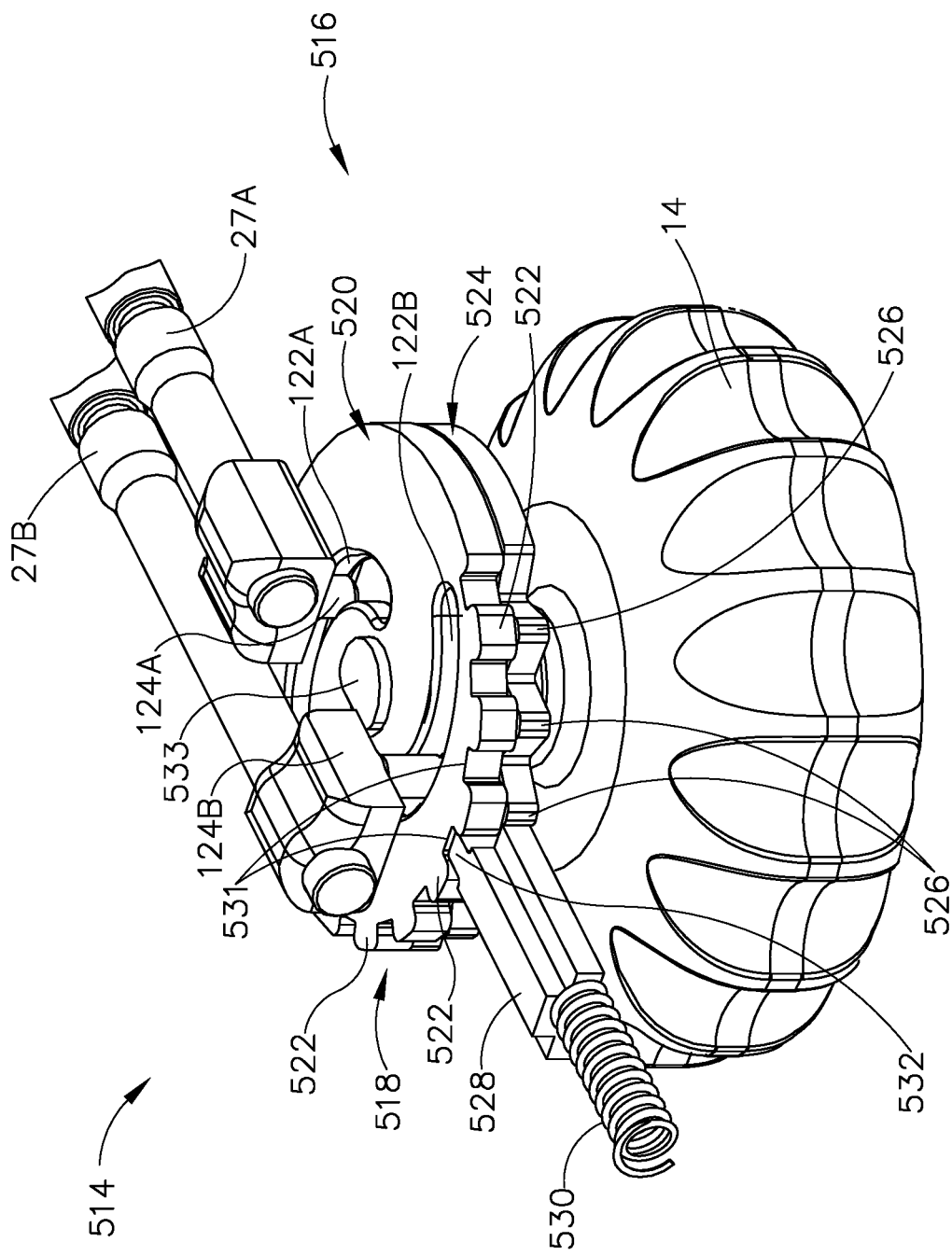
FIG. 32 depicts a perspective view of the joint stabilization drive assembly of FIG. 31 including a lock mechanism.

With respect to FIG. 29-30B, rotating rotary knob (14) similarly rotates disk (422) and guides movement of cam followers (124A, 124B) along cam slots (122A, 122B) as discussed above. Detent notches (424) and detent abutment (428) of the present example are collectively positioned to correspond to one of a plurality of predetermined positions of knob (14) and alignment of cartridge receiving assembly (50) (see FIG. 7A) along longitudinal axis (LA). Thus, detent notches (424) resiliently and releasably capture detent abutment (428) to arrest actuation of disk (422) and, in turn, cartridge receiving assembly (50) (see FIG. 7A). Furthermore, in the present example, biasing detent (420) generates tactile and/or audible feedback to simultaneously indicate to the operator that knob (14) is in one of a plurality of predetermined positions as discussed above with respect to various detent position indicators (218, 282). Outer drive stabilization indicator (416) is thereby configured to indicate one or more predetermined positions to the operator during use. Outer drive stabilization indicator (416) is thus not intended to be unnecessarily limited to only one of stabilization or positioning.

D. Fourth Example of an Articulation Control Assembly with a Joint Stabilization Drive Assembly FIGS. 31-39D, show a portion of a housing (512) receiving a fourth example of an articulation control assembly (514) with a joint stabilization drive assembly (516). With respect to FIGS. 31-32, joint stabilization drive assembly (516) has a joint stabilizer (518) configured to arrest actuation of a cam disk (520) and thereby inhibit articulation of cartridge receiving assembly (50) (see FIG. 7A) relative to shaft (20) (see FIG. 7A). To this end, joint stabilization drive assembly (516) is similar to joint drive assembly (118) (see FIG. 3) with rods (27A, 27B) having cam followers (124A, 124B) received within cam slots (127A, 127B) in cam disk (520). As will be described in more detail below, joint stabilizer (518) generally secures articulation joint (23) (see FIG. 7A) in one of a plurality of articulation positions until the operator selectively rotates rotary knob (14). Rotation of rotary knob (14) causes joint stabilizer (518) to transition from a locked state to an unlocked state, thereby transmitting further selective rotation of the rotary knob (14) to cam disk (520). Thus, joint stabilization drive assembly (516) is configured to articulate articulation joint (23) (see FIG. 7A) as discussed above; but joint stabilizer (518) in the locked state is configured to seize cam disk (520) when not being manipulated by the operator in order to prevent inadvertent movement of cartridge receiving assembly (50) (see FIG. 7A) at articulation joint (23) (see FIG. 7A).

It should be appreciated that housing (512) may additionally include a variety of manual actuators including but not limited to a manual pistol grip handle, a scissor grip handle, a syringe grip handle, endoscopic rotary knobs, and the like. Housing (512) could also take the form of a robotic interface, such as a DAVINCI puck, or a housing comprising gears or pulleys, servomechanisms, and the like. Thus, joint stabilizer (518) and, indeed, any such joint stabilizers and/or position indicators may be incorporated into a wide variety of handle assemblies for use with a wide variety of shaft assemblies generally contemplated herein. The invention is thus not intended to be unnecessarily limited to the particular surgical instrument (2) (see FIG. 1) described herein.

Figure 33:
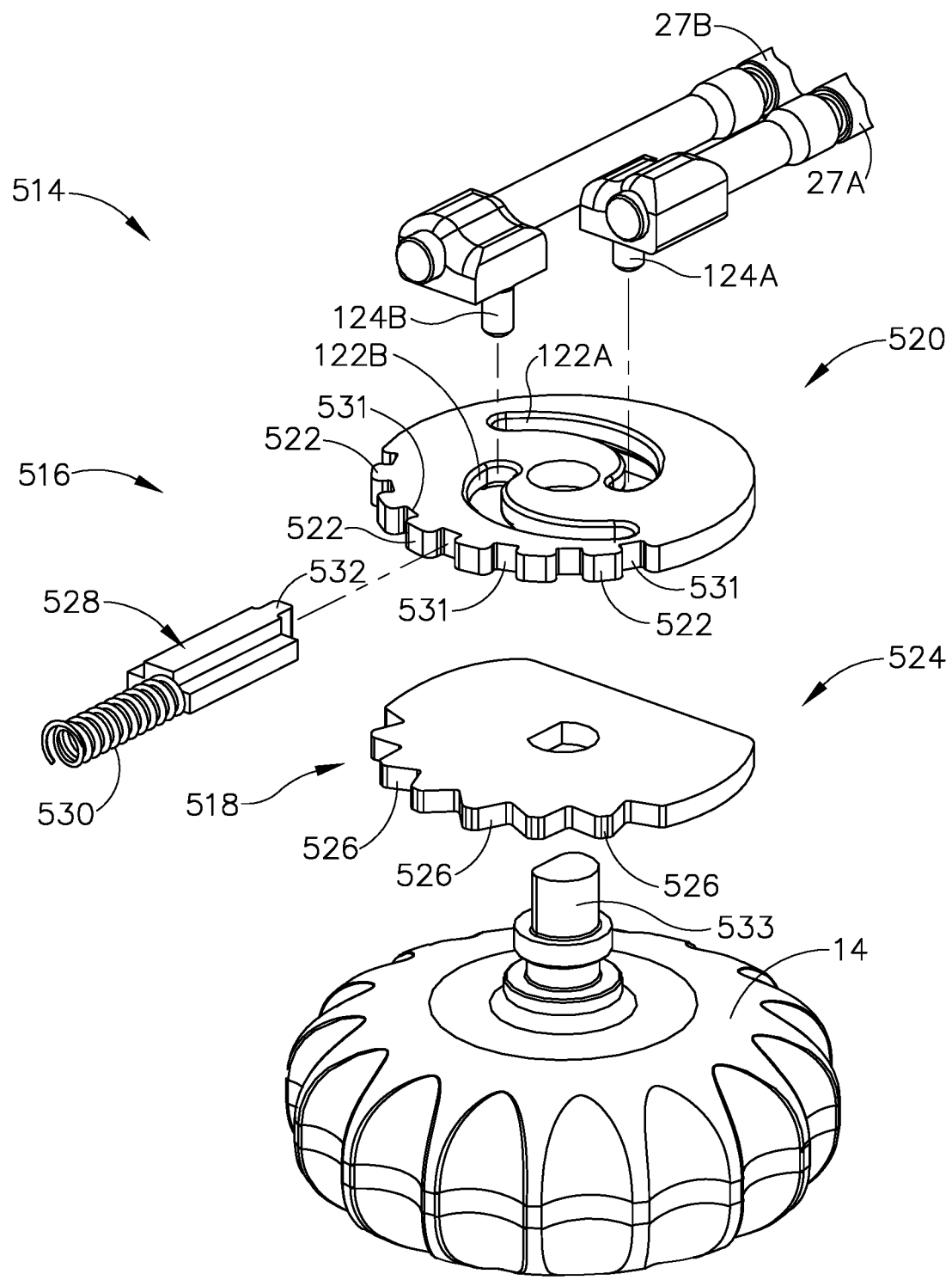
FIG. 33 depicts a partially exploded perspective view of the joint stabilization drive assembly of FIG. 32 including a cam disk, a cam plate, and a lock bar of the lock mechanism.
Figure 34:
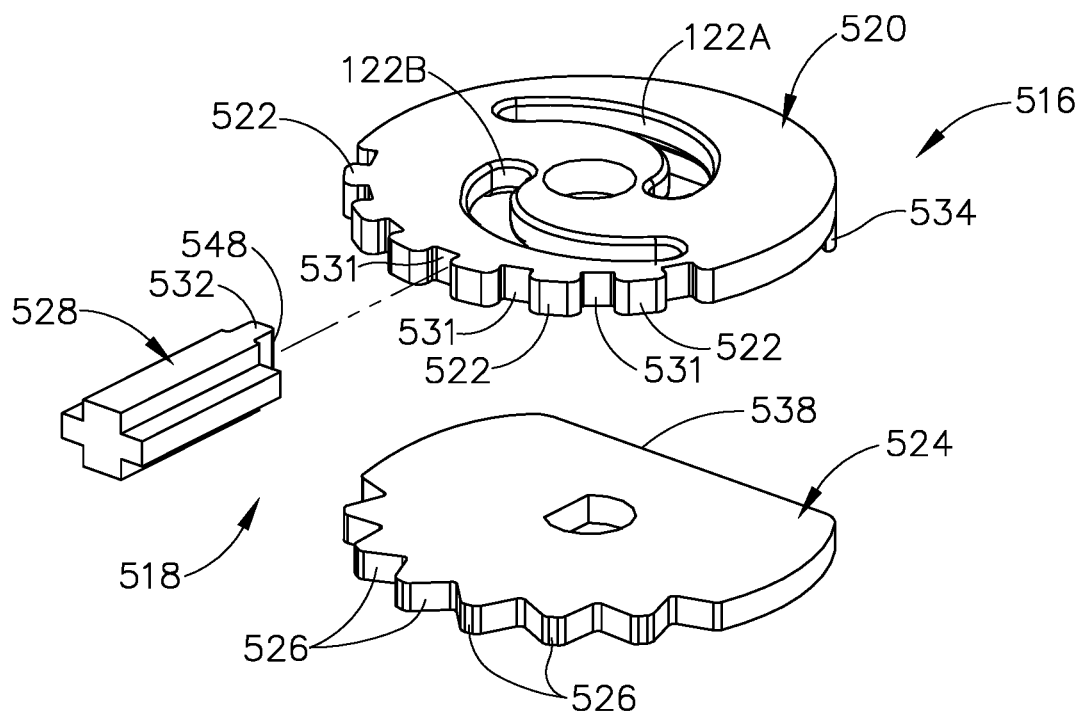
FIG. 34 depicts an exploded, upper perspective view of the cam disk, the cam plate, and the lock bar of FIG. 33.
Figure 35:
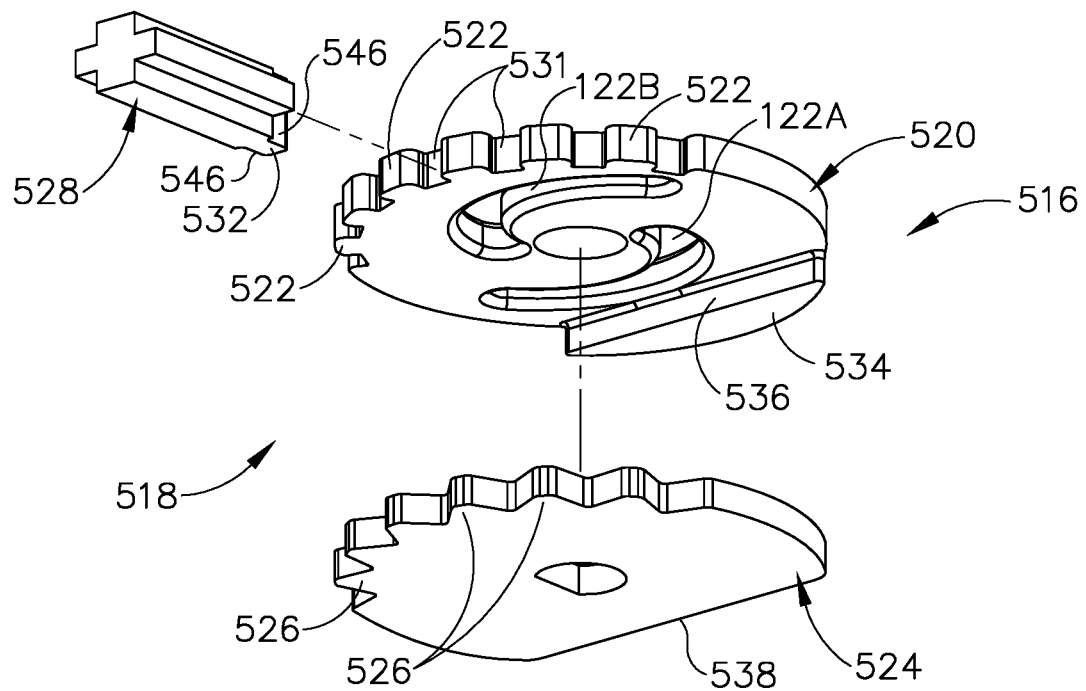
FIG. 35 depicts an exploded, lower perspective view of the cam disk, the cam plate, and the lock bar of FIG. 33.
Figure 36:
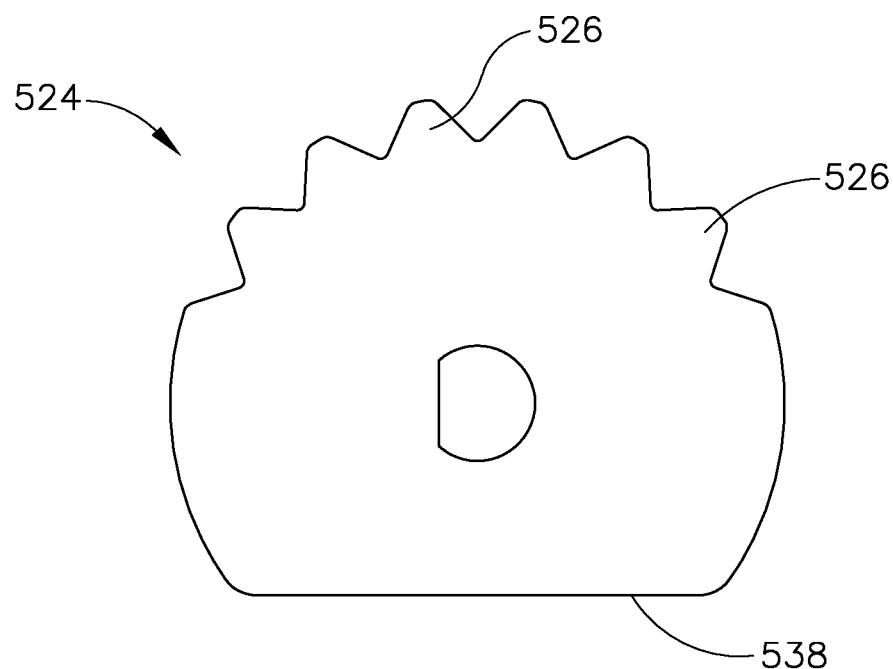
FIG. 36 depicts a bottom plan view of the cam plate of FIG. 33.
Figure 37:
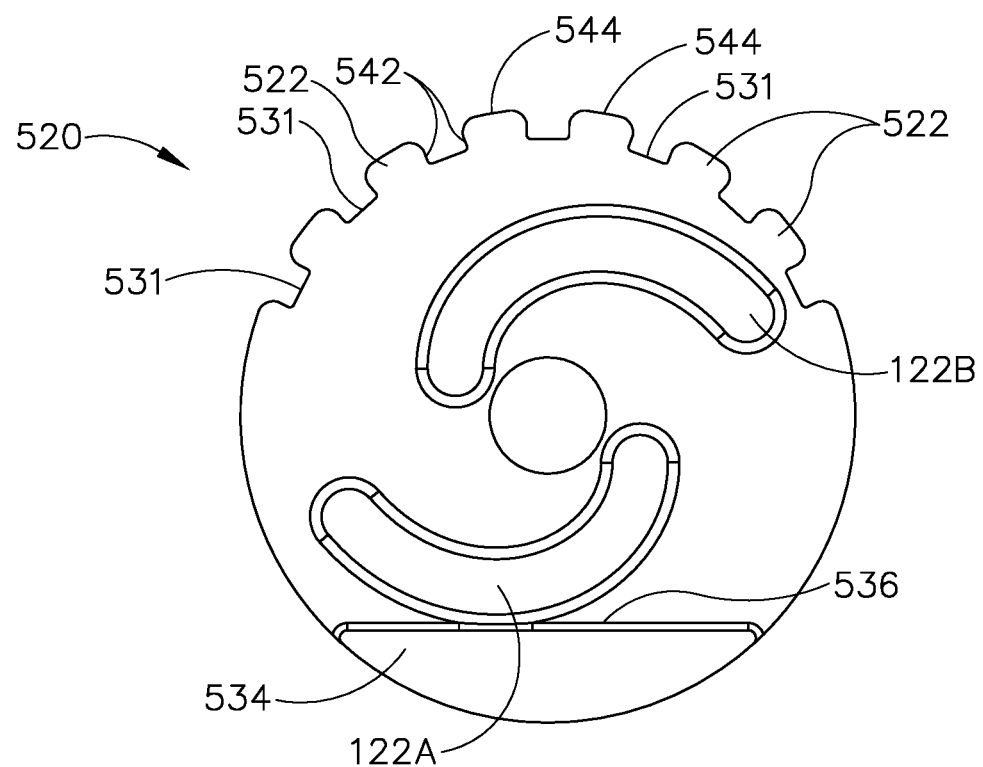
FIG. 37 depicts a bottom plan view of the cam disk of FIG. 33.

FIGS. 33-35 show joint stabilization drive assembly (516) with joint stabilizer (518) in greater detail. In addition to cam disk (520) having a plurality of first cam teeth (522), joint stabilizer (518) further includes a cam plate (524) having a plurality of second cam teeth (526) and a lock bar (528) resiliently biased via a spring (530). First cam teeth (522) defining a plurality of detent notches (531), and lock bar (528) has a detent abutment (532) extending distally therefrom. In the locked state, detent abutment (532) is received within detent notch (531) to arrest movement of cam plate (524), whereas, in the unlocked state, detent abutment (532) is removed from detent notch (531) to allow movement of cam plate (524). In the present example, lock bar (528) is biased by spring (530) toward the locked state to engage detent abutment (532) against cam disk (520) and cam plate (524) within detent notch (531), but may be urged from detent notch (531) via cam plate (524) toward the unlocked state as discussed below. Detent abutment (532) may also be referred to herein as a lock tooth (532). The terms "lock tooth" and "detent abutment" are thus interchangeable in the present example, and the invention is not intended to be unnecessarily limited to the particular lock tooth (532) shown and described herein.

Cam disk (520) is stacked on a cam plate (524) such that cam disk (520) and cam plate (524) are nested together and received on a cam holding pin (533), which extends rigidly upward from rotary knob (14). Cam plate (524) is rotatably keyed to cam holding pin (533), whereas cam disk (520) is free to rotate relative to cam holding pin (533). Thus, cam disk (230) is rotationally coupled with cam holding pin (533). While cam disk (520) is configured to have some relative rotation relative to cam plate (524), such relative rotation, also referred to herein as "slip," is limited to transfer rotation from cam plate (524) to cam disk (520). With respect to FIGS. 35-37, cam disk (520) further includes a downwardly projecting boss (534) having a boss flat (536), and cam plate (524) has a corresponding plate flat (538). Boss flat (536) in the locked state is generally offset from plate flat (536) defining a radial gap (540) (see FIG. 39A) between cam plate (524) and boss (534). However, as cam plate (524) slips relative to cam disk (520) in either clockwise or counterclockwise directions, plate flat (536) eventually closes radial gap (540) (see FIG. 39A) to engage boss flat (536). Once engaged, cam plate (524) is configured to urge rotation of cam disk (520) from the locked state toward the unlocked state.

As shown in FIGS. 36-38A and FIG. 39A, each tooth (522) of first cam teeth (522) has generally straight parallel sides (542) and an outer radial surface (544). Lock tooth (532) has generally straight parallel sides (546) that are operable to fit between first cam teeth (522) and second cam teeth (526). The distal end of lock tooth (532) has a rounded tip (548) with parallel sides (546) configured to engage parallel sides (542) to prevent lock tooth (532) from riding along first cam teeth (522) without assistance from cam plate (524). This engagement between at least one side (542) and at least one side (546) also prevents translation of cam followers (124A, 124B) received within cam slots (127A, 127B) in cam disk (418), thereby preventing cartridge receiving assembly (50) (see FIG. 7A) from pivoting at articulation joint (23) (see FIG. 7A).

Figure 38A:
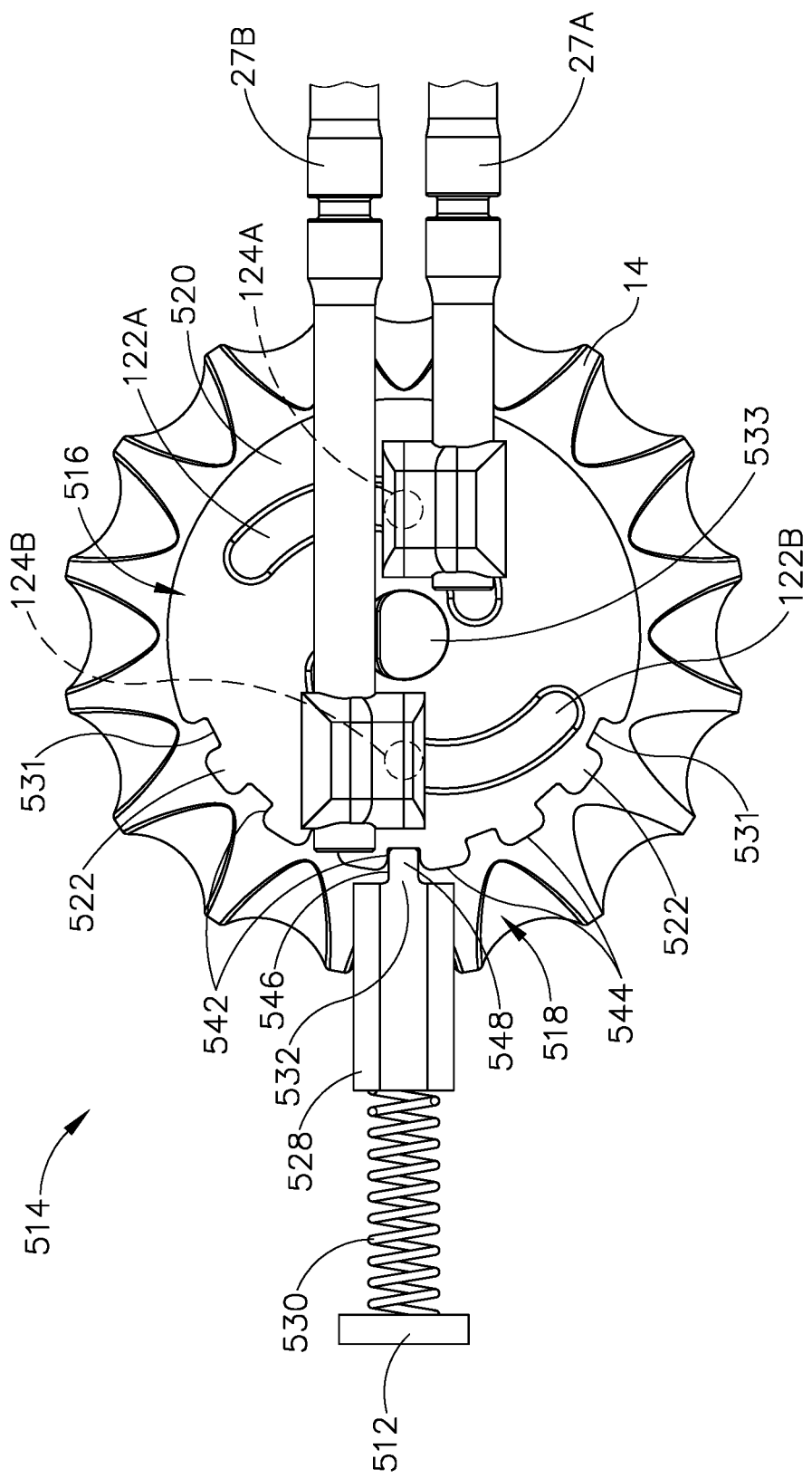
FIG. 38A depicts an enlarged top plan view of the joint stabilization drive assembly of FIG. 32 in a center position and the cam disk locked.
Figure 38B:
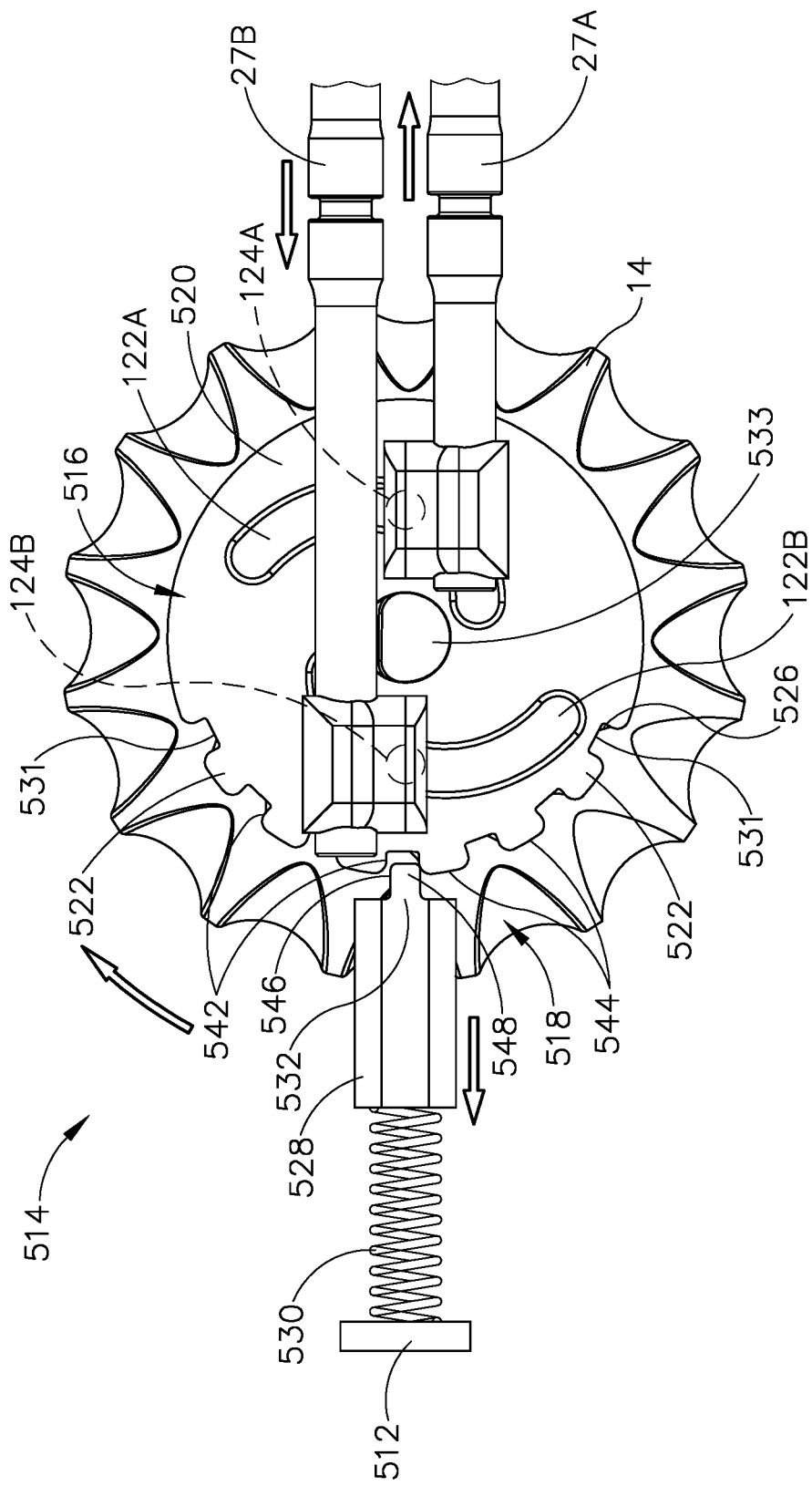
FIG. 38B depicts the enlarged top plan view of the joint stabilization drive assembly similar to FIG. 38A, but showing a rotary knob rotating clockwise such that the cam gear unseats the lock bar from the cam disk to unlock the cam disk for rotating the cam disk from the center position toward a right position.
Figure 38C:
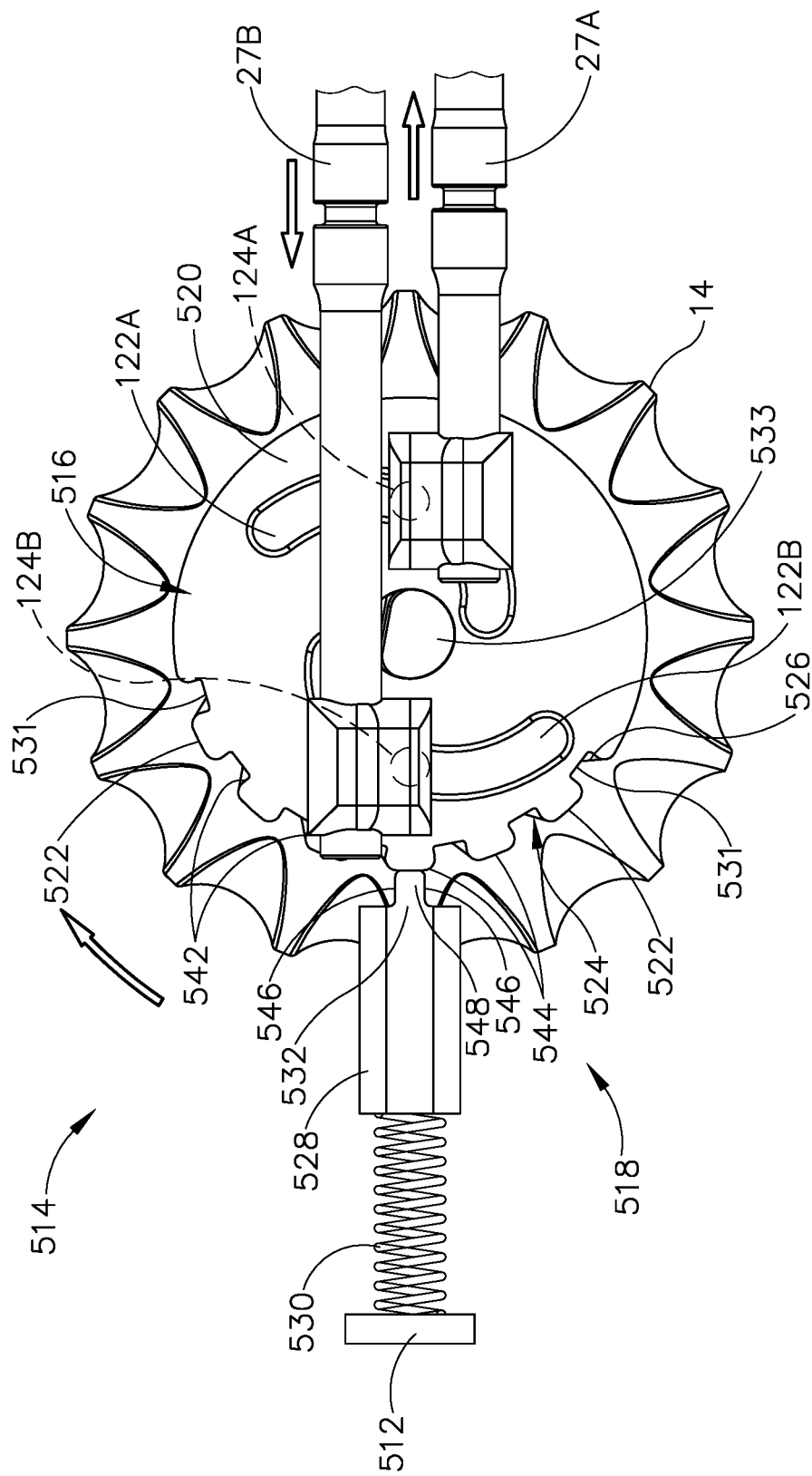
FIG. 38C depicts the enlarged top plan view of the joint stabilization drive assembly similar to FIG. 38B, but showing the rotary knob further rotating clockwise such that the lock bar slides along the cam disk and rotates further toward the right position.
Figure 39A:
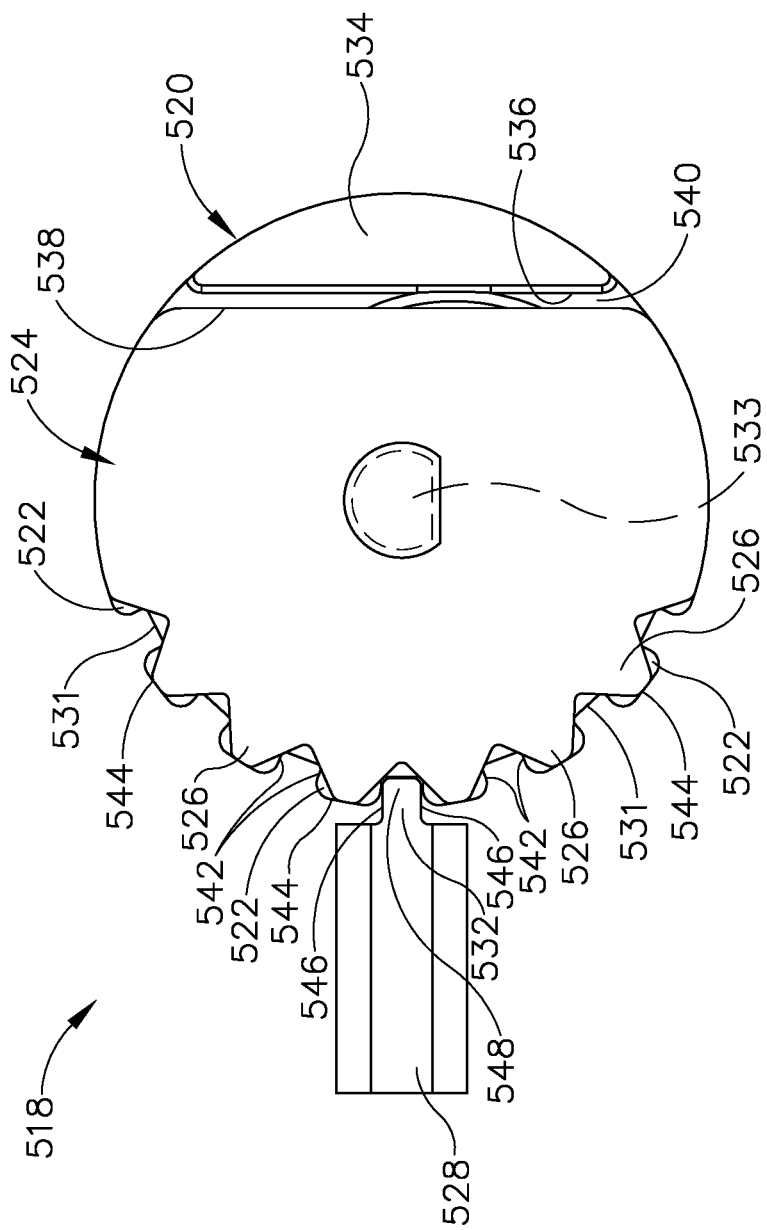
FIG. 39A depicts an enlarged bottom plan view of the joint stabilization drive assembly of FIG. 38A in the center position and the cam disk locked.
Figure 39B:
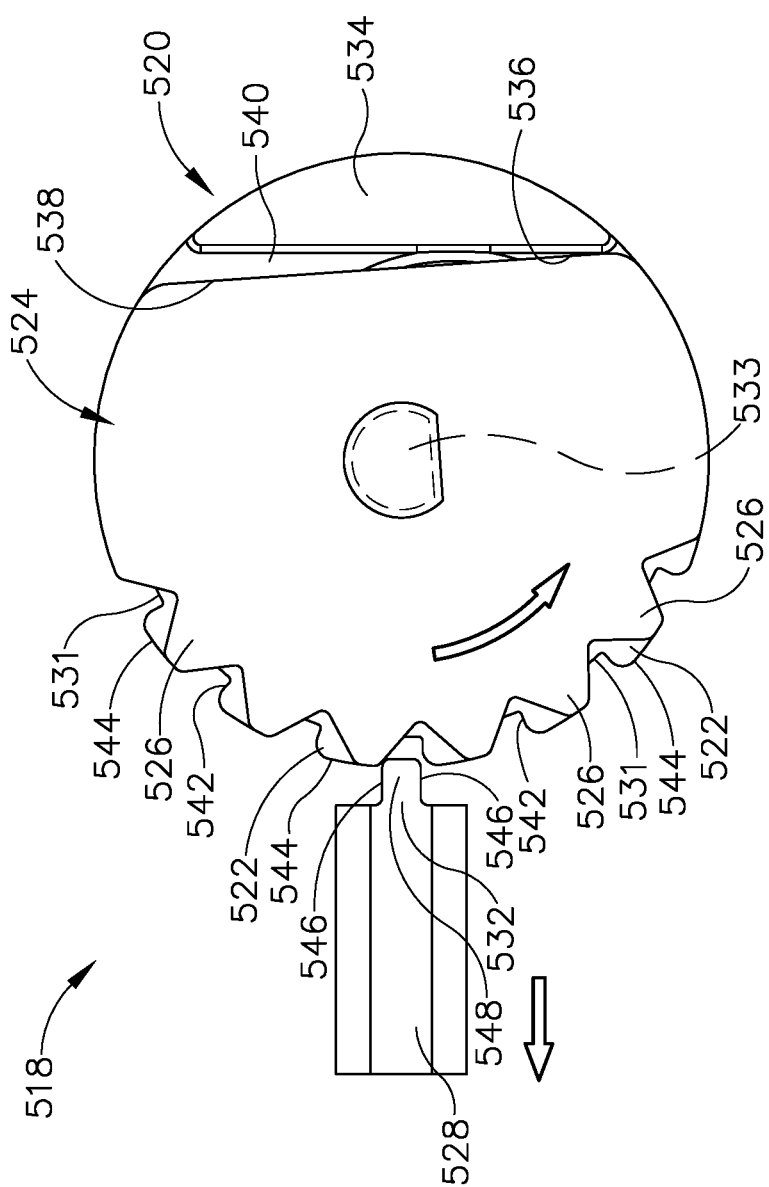
FIG. 39B depicts the enlarged bottom plan view of the joint stabilization drive assembly similar to FIG. 39A, but showing the the cam gear unseating the lock bar from the cam disk to unlock the cam disk for rotating the cam disk from the center position toward a right position.
Figure 39C:
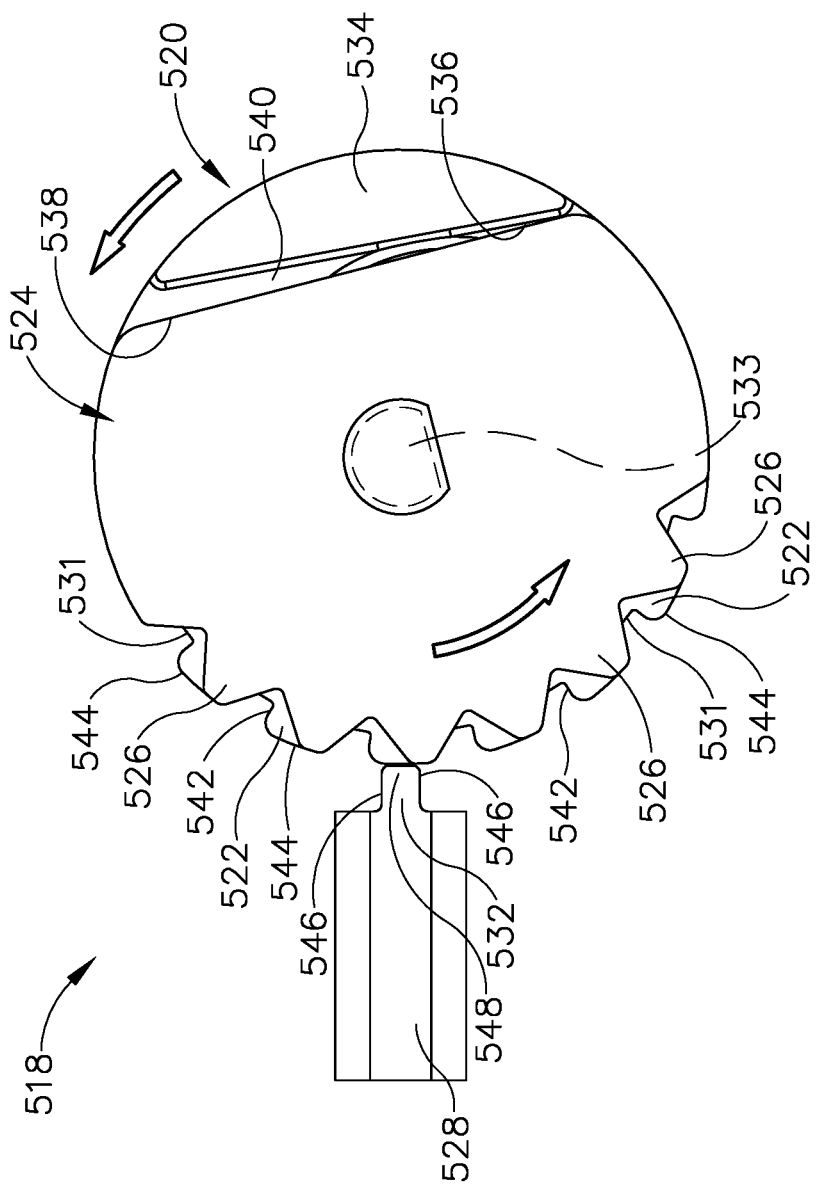
FIG. 39C depicts the enlarged top plan view of the joint stabilization drive assembly similar to FIG. 39B, but showing the lock bar sliding along cam disk and rotating further toward the right position.

Second cam teeth (526) of cam plate (524) are each a rounded triangular tooth (526) configured to cam against rounded tip (548) of lock tooth (532). As shown in FIG. 38B and FIG. 39B, second cam teeth (524) thereby drive lock bar (528) proximally in response rotary knob (14) directing rotation of cam plate (524). It should be understood that tooth (526) may have a variety of different shapes other than triangular. Lock tooth (532) moves proximally sufficiently such that rounded tip (548) of lock tooth (532) can then eventually engage and ride along outer radial surface (544) of first cam teeth (522) as cam disk (520) and cam plate (524) collectively continue to rotate with lock bar (528) in the unlocked state as shown in FIG. 38C and FIG. 39C.

Figure 38D:
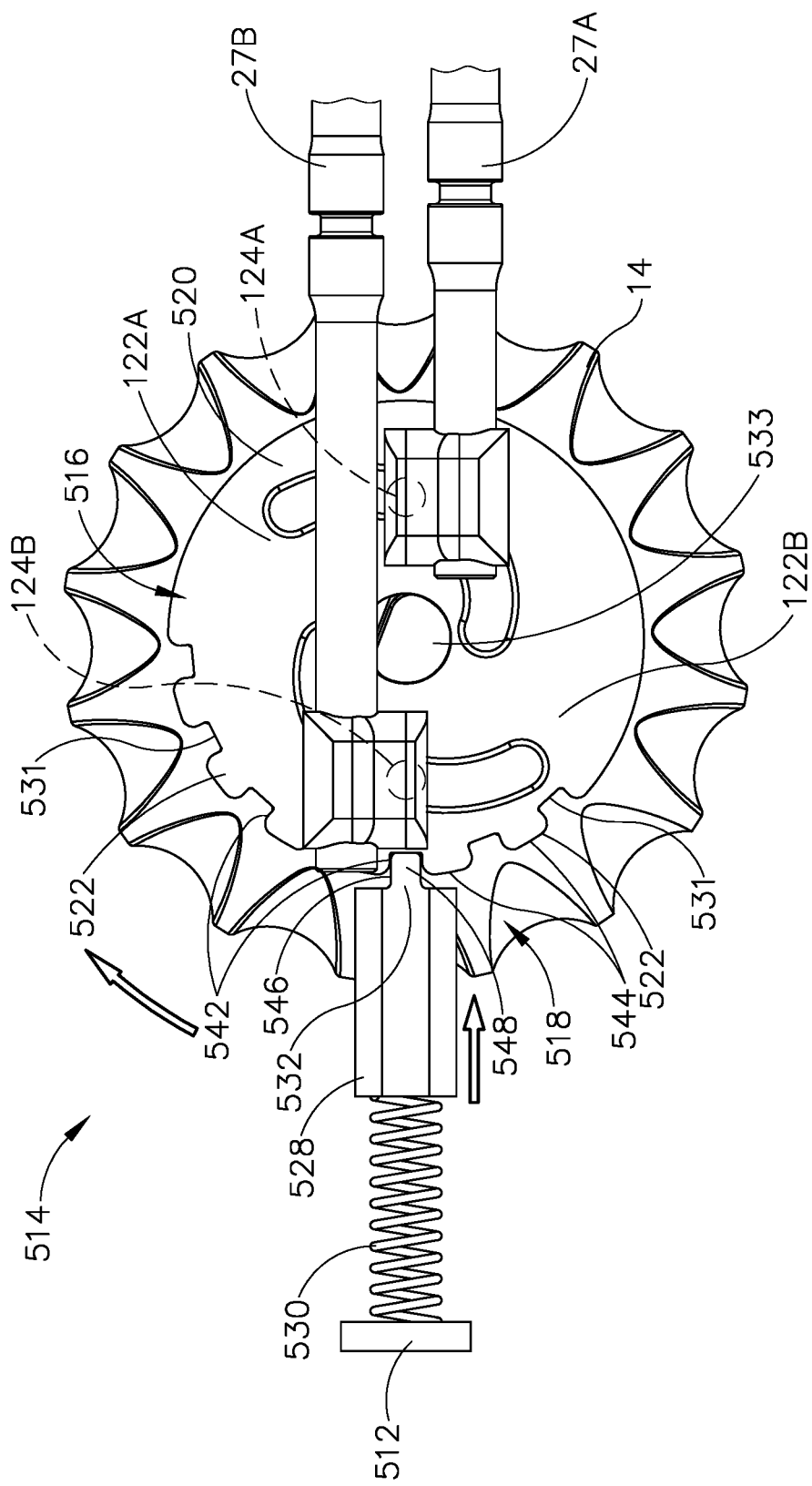
FIG. 38D depicts the enlarged top plan view of the joint stabilization drive assembly similar to FIG. 38C, but showing the rotary knob further rotated clockwise such that the lock bar seats against the cam gear and the cam disk to lock the cam disk in the right position.
Figure 39D:
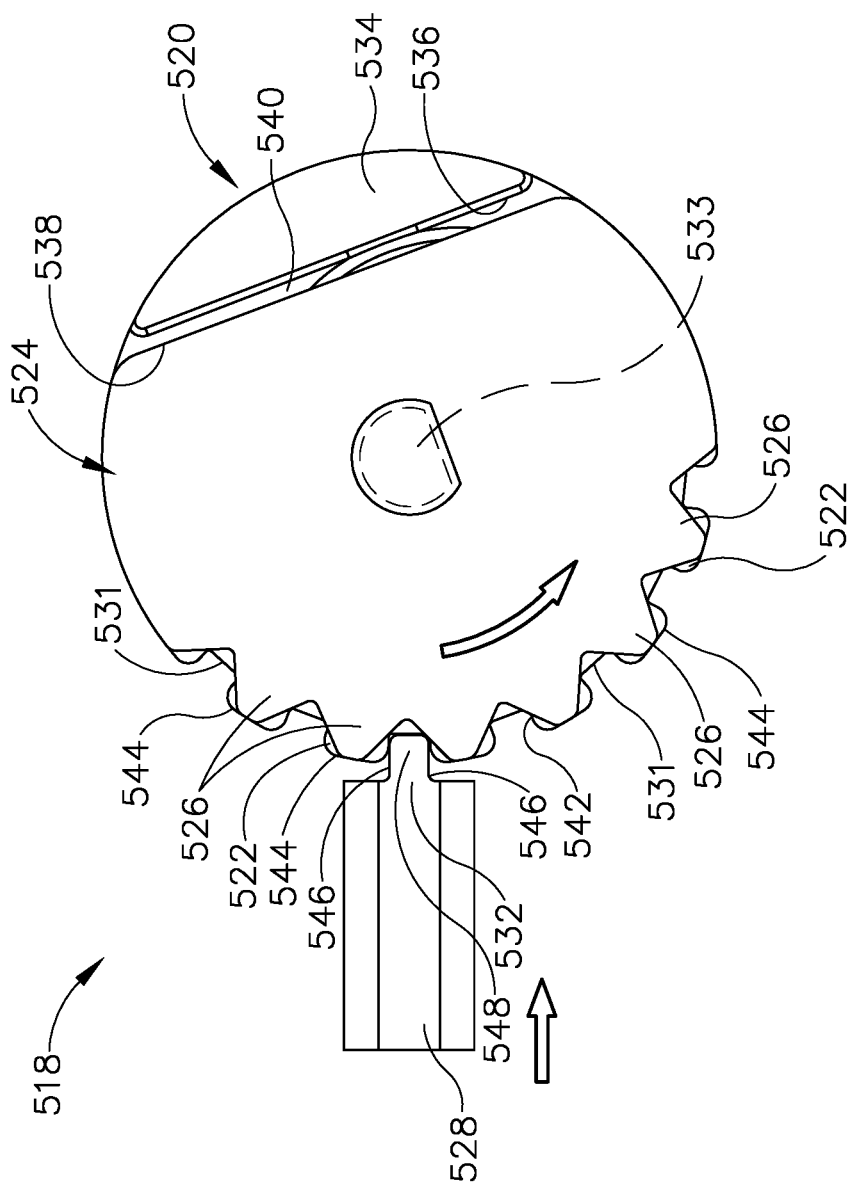
FIG. 39D depicts the enlarged top plan view of the joint stabilization drive assembly similar to FIG. 39C, but showing the lock bar seated against the cam gear and the cam disk to lock the cam disk in the right position.

Once lock tooth (532) traverses outer radial surface (544) of cam disk (520) and triangular tooth (526) of cam plate (524), then lock tooth (532) returns distally to a position between the next pair of first cam teeth (522) and second cam teeth (526) similar to the positioning shown in FIG. 38D and FIG. 39D. For illustrative purposes, advancing lock tooth (532) between one set of first cam teeth (522) and second cam teeth (526) to an adjacent set of first cam teeth (522) and second cam teeth (526) may be considered one articulation increment. As lock tooth (532) distally advances, lock tooth (532) strikes cam disk (520) between first cam teeth (522) to generate tactile and/or audible feedback similar to various indicators discussed above. It will be understood that lock tooth (532) need not necessarily extend far enough to strike cam disk (520). For instance, lock tooth (532) may only extend distally such that parallel sides (542, 546) prevent lock tooth (546) from riding along cam disk (520) without assistance from cam plate (524). In the illustrated version, bosses (not shown) are configured to prevent further distal motion of lock bar (532). Another example of such teeth (522, 526, 532) configured to lock and unlock articulation of a joint are shown and described U.S. Pat. No. 9,186,142, entitled "Surgical Instrument End Effector Articulation Drive with Pinion and Opposing Racks," issued Nov. 17, 2015, the disclosure of which is incorporated by reference herein III. Exemplary Combinations The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft assembly, including: (i) a proximal end portion, (ii) a distal end portion, wherein the distal end portion is configured drive a needle through tissue, and (iii) an articulation joint, wherein the articulation joint is operable to selectively articulate the distal end portion relative to the proximal end portion; and (b) a body assembly extending proximally from the shaft assembly and including: (i) a joint drive assembly operatively connected to the articulation joint and configured to actuate the articulation to thereby articulate the distal end portion relative to the proximal end portion, (ii) an actuator configured to actuate the joint drive assembly for articulating the articulation joint, and (iii) a joint stabilizer including a detent abutment and a detent notch, wherein the detent abutment and the detent notch are operatively connected to the actuator and the joint drive assembly such that the detent notch is configured to releasably capture the detent abutment to arrest actuation of the joint drive assembly and thereby inhibit articulation of the distal end portion of the shaft assembly relative to the proximal end portion of the shaft assembly.

Example 2

The surgical instrument of Example 1, wherein the joint drive assembly further includes a disk operatively connected between the articulation joint and the actuator, wherein the detent notch is positioned on the disk.

Example 3

The surgical instrument of Example 2, wherein the disk includes a cam slot having a length component and a radial component such that the cam slot spirals radially outward, and wherein the detent notch is positioned along cam slot.

Example 4

The surgical instrument of Example 3, wherein the joint drive assembly further includes a rod and a cam follower extending from the rod, wherein the cam follower is received within the cam slot and the rod extends toward the articulation joint to transmit motion from the cam follower to the articulation joint, wherein the detent abutment is positioned on the cam follower.

Example 5

The surgical instrument of Example 2, wherein the disk includes an outer circumferential surface, and wherein the detent notch is positioned on the outer circumferential surface.

Example 6

The surgical instrument of Example 5, wherein the body assembly further includes a housing containing the joint drive assembly, the actuator, and the joint stabilizer, and wherein the detent abutment projects from the housing and is resiliently engaged with the disk.

Example 7

The surgical instrument of Example 6, wherein the joint drive assembly further includes a rod and a cam follower extending from the rod, wherein the cam follower is received within the cam slot and the rod extends toward the articulation joint to transmit motion from the cam follower to the articulation joint.

Example 8

The surgical instrument of Example 5, wherein the joint stabilizer further includes a cam plate, a lock bar having the detent abutment, and the disk is a cam disk having the detent notch, wherein the lock bar is engaged with the cam plate and the cam disk in the detent notch to inhibit movement of the cam disk in a locked position, wherein the cam plate is operatively connected to the actuator and configured to be rotatably driven by the actuator to thereby urge the lock plate toward an unlocked position, and wherein the cam plate is further configured to urge rotation of the cam disk with the lock bar in the unlocked position for articulating the articulation joint.

Example 9

The surgical instrument of Example 8, wherein the cam plate is nested against the cam disk to define a radial gap therebetween such that the cam plate rotatably slips relative to the cam disk to urge the lock bar from the locked position toward the unlocked position.

Example 10

The surgical instrument of Example 9, wherein at least a portion of the radial gap is configured to close as the cam plate slips relative to the cam disk such that the cam plate engages the cam disk with the lock bar in the unlocked position for urging rotation of the cam disk.

Example 11

The surgical instrument of Example 1, wherein the joint stabilizer further includes a biasing detent defining the detent notch, and wherein the biasing detent is secured to disk.

Example 12

The surgical instrument of Example 1, wherein the detent abutment and the detent notch at least partially define a detent position indicator operatively keyed to a predetermined position of the distal end portion of the shaft assembly relative to the proximal end portion of the shaft assembly, wherein the detent abutment is configured to engage the detent notch and tactilely generate a position feedback thereby indicating the predetermined position to the operator.

Example 13

The surgical instrument of any one or more of Examples 1 through 12, wherein the actuator includes a rotary knob configured to selectively rotate about an axis.

Example 14

The surgical instrument of Example 13, wherein the rotary knob has a position indicator extending therefrom, wherein the position indicator on the rotary knob is operatively keyed to a predetermined position of the distal end portion of the shaft assembly relative to the proximal end portion of the shaft assembly, and wherein the position indicator is configured to visually or tactilely provide a position feedback to indicate the predetermined position to an operator.

Example 15

The surgical instrument of Example 14, wherein the rotary knob is configured to rotate about an axis, and wherein the position indicator extends radially outward relative to the axis further than a remainder of the rotary knob.

Example 16

A surgical instrument, comprising: (a) a shaft assembly, including: (i) a proximal end portion, (ii) a distal end portion, wherein the distal end portion is configured to drive a needle through tissue, and (iii) an articulation joint, wherein the articulation joint is operable to selectively articulate the distal end portion relative to the proximal end portion to a predetermined position from another position; (b) a body assembly extending proximally from the shaft assembly and including: (i) a joint drive assembly having a cam disk operatively connected to the articulation joint and configured to actuate the articulation joint to thereby articulate the distal end portion relative to the proximal end portion, (ii) an actuator, and (iii) a joint stabilizer including: (A) a cam plate operatively connected to the actuator and configured to engage the cam disk, (B) a lock bar configured to move from a locked position to an unlocked position, wherein the lock bar in the locked position is configured to engage the cam disk to inhibit movement of the cam disk, and wherein the lock bar in the unlocked position is configured to release movement of the cam disk, wherein the cam plate is configured to urge the lock bar from the locked position to the unlocked position and then further urge the cam disk of the joint drive assembly to rotate and thereby actuate the articulation joint with the lock bar in the unlocked position.

Example 17

The surgical instrument of Example 16, wherein the cam plate is nested against the cam disk to define a radial gap therebetween such that the cam plate rotatably slips relative to the cam disk to urge the lock bar from the locked position toward the unlocked position.

Example 18

The surgical instrument of Example 17, wherein at least a portion of the radial gap is configured to close as the cam plate slips relative to the cam disk such that the cam plate engages the cam disk with the lock bar in the unlocked position for urging rotation of the cam disk.

Example 19

A surgical instrument, comprising: (a) a shaft assembly, including: (i) a proximal end portion, (ii) a distal end portion, wherein the distal end portion is configured to drive a needle through tissue, and (iii) an articulation joint, wherein the articulation joint is operable to selectively articulate the distal end portion relative to the proximal end portion to a predetermined position from another position; (b) a body assembly extending proximally from the shaft assembly and including: (i) a joint drive assembly operatively connected to the articulation joint and configured to actuate the articulation to thereby articulate the distal end portion relative to the proximal end portion, (ii) a rotary knob configured to actuate the joint drive assembly for articulating the articulation joint, and (iii) a position indicator extending from the rotary knob and operatively keyed to the predetermined position of the distal end portion of the shaft assembly relative to the proximal end portion of the shaft assembly, and wherein the position indicator is configured to provide a position feedback to indicate the predetermined position to an operator.

Example 20

The surgical instrument of Example 21, wherein the position indicator is configured to visually or tactilely provide the position feedback to indicate the predetermined position to an operator.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
    (a) a shaft assembly, including:
        (i) a proximal end portion,
        (ii) a distal end portion, wherein the distal end portion is configured drive a needle through tissue, and
        (iii) an articulation joint, wherein the articulation joint is operable to selectively articulate the distal end portion relative to the proximal end portion; and
    (b) a body assembly extending proximally from the shaft assembly and including:
        (i) a joint drive assembly operatively connected to the articulation joint and configured to actuate the articulation to thereby articulate the distal end portion relative to the proximal end portion,
        (ii) an actuator configured to actuate the joint drive assembly for articulating the articulation joint, and
        (iii) a joint stabilizer including a detent abutment and a detent notch, wherein the detent abutment and the detent notch are operatively connected to the actuator and the joint drive assembly such that the detent notch is configured to releasably capture the detent abutment to arrest actuation of the joint drive assembly and thereby inhibit articulation of the distal end portion of the shaft assembly relative to the proximal end portion of the shaft assembly.

2. The surgical instrument of claim 1, wherein the joint drive assembly further includes a disk operatively connected between the articulation joint and the actuator, wherein the detent notch is positioned on the disk.

3. The surgical instrument of claim 2, wherein the disk includes a cam slot having a length component and a radial component such that the cam slot spirals radially outward, and wherein the detent notch is positioned along cam slot.

4. The surgical instrument of claim 3, wherein the joint drive assembly further includes a rod and a cam follower extending from the rod, wherein the cam follower is received within the cam slot and the rod extends toward the articulation joint to transmit motion from the cam follower to the articulation joint, wherein the detent abutment is positioned on the cam follower.

5. The surgical instrument of claim 2, wherein the disk includes an outer circumferential surface, and wherein the detent notch is positioned on the outer circumferential surface.

6. The surgical instrument of claim 5, wherein the body assembly further includes a housing containing the joint drive assembly, the actuator, and the joint stabilizer, and wherein the detent abutment projects from the housing and is resiliently engaged with the disk.

7. The surgical instrument of claim 6, wherein the joint drive assembly further includes a rod and a cam follower extending from the rod, wherein the cam follower is received within the cam slot and the rod extends toward the articulation joint to transmit motion from the cam follower to the articulation joint.

8. The surgical instrument of claim 5, wherein the joint stabilizer further includes a cam plate, a lock bar having the detent abutment, and the disk is a cam disk having the detent notch, wherein the lock bar is engaged with the cam plate and the cam disk in the detent notch to inhibit movement of the cam disk in a locked position, wherein the cam plate is operatively connected to the actuator and configured to be rotatably driven by the actuator to thereby urge the lock plate toward an unlocked position, and wherein the cam plate is further configured to urge rotation of the cam disk with the lock bar in the unlocked position for articulating the articulation joint.

9. The surgical instrument of claim 8, wherein the cam plate is nested against the cam disk to define a radial gap therebetween such that the cam plate rotatably slips relative to the cam disk to urge the lock bar from the locked position toward the unlocked position.

10. The surgical instrument of claim 9, wherein at least a portion of the radial gap is configured to close as the cam plate slips relative to the cam disk such that the cam plate engages the cam disk with the lock bar in the unlocked position for urging rotation of the cam disk.

11. The surgical instrument of claim 1, wherein the joint stabilizer further includes a biasing detent defining the detent notch, and wherein the biasing detent is secured to disk.

12. The surgical instrument of claim 1, wherein the detent abutment and the detent notch at least partially define a detent position indicator operatively keyed to a predetermined position of the distal end portion of the shaft assembly relative to the proximal end portion of the shaft assembly, wherein the detent abutment is configured to engage the detent notch and tactilely generate a position feedback thereby indicating the predetermined position to the operator.

13. The surgical instrument of claim 1, wherein the actuator includes a rotary knob configured to selectively rotate about an axis.

14. The surgical instrument of claim 13, wherein the rotary knob has a position indicator extending therefrom, wherein the position indicator on the rotary knob is operatively keyed to a predetermined position of the distal end portion of the shaft assembly relative to the proximal end portion of the shaft assembly, and wherein the position indicator is configured to visually or tactilely provide a position feedback to indicate the predetermined position to an operator.

15. The surgical instrument of claim 14, wherein the rotary knob is configured to rotate about an axis, and wherein the position indicator extends radially outward relative to the axis further than a remainder of the rotary knob.

16. A surgical instrument, comprising:
(a) a shaft assembly, including:
   (i) a proximal end portion,
   (ii) a distal end portion, wherein the distal end portion is configured to drive a needle through tissue, and
   (iii) an articulation joint, wherein the articulation joint is operable to selectively articulate the distal end portion relative to the proximal end portion to a predetermined position from another position;
(b) a body assembly extending proximally from the shaft assembly and including:
   (i) a joint drive assembly having a cam disk operatively connected to the articulation joint and configured to actuate the articulation joint to thereby articulate the distal end portion relative to the proximal end portion,
   (ii) an actuator, and
   (iii) a joint stabilizer including:
      (A) a cam plate operatively connected to the actuator and configured to engage the cam disk,
      (B) a lock bar configured to move from a locked position to an unlocked position, wherein the lock bar in in the locked position is configured to engage the cam disk to inhibit movement of the cam disk, and wherein the lock bar in the unlocked position is configured to release movement of the cam disk,
   wherein the cam plate is configured to urge the lock bar from the locked position to the unlocked position and then further urge the cam disk of the joint drive assembly to rotate and thereby actuate the articulation joint with the lock bar in the unlocked position.

17. The surgical instrument of claim 16, wherein the cam plate is nested against the cam disk to define a radial gap therebetween such that the cam plate rotatably slips relative to the cam disk to urge the lock bar from the locked position toward the unlocked position.

18. The surgical instrument of claim 17, wherein at least a portion of the radial gap is configured to close as the cam plate slips relative to the cam disk such that the cam plate engages the cam disk with the lock bar in the unlocked position for urging rotation of the cam disk.

19. A surgical instrument, comprising:
(a) a shaft assembly, including:
   (i) a proximal end portion,
   (ii) a distal end portion, wherein the distal end portion is configured to drive a needle through tissue, and
   (iii) an articulation joint, wherein the articulation joint is operable to selectively articulate the distal end portion relative to the proximal end portion to a predetermined position from another position;
(b) a body assembly extending proximally from the shaft assembly and including:
   (i) a joint drive assembly operatively connected to the articulation joint and configured to actuate the articulation to thereby articulate the distal end portion relative to the proximal end portion,
   (ii) a rotary knob configured to actuate the joint drive assembly for articulating the articulation joint, and
   (iii) a position indicator extending from the rotary knob and operatively keyed to the predetermined position of the distal end portion of the shaft assembly relative to the proximal end portion of the shaft assembly, and wherein the position indicator is configured to provide a position feedback to indicate the predetermined position to an operator,
   wherein the rotary knob is configured to rotate about an axis, and wherein the position indicator extends radially outwardly relative to the axis further than a remainder of the rotary knob.

20. The surgical instrument of claim 19, wherein the position indicator is configured to visually or tactilely provide the position feedback to indicate the predetermined position to an operator.

* * * * *